(12) United States Patent
Baselga et al.

(10) Patent No.: US 9,566,334 B2
(45) Date of Patent: Feb. 14, 2017

(54) COMBINATIONS OF A PI3K/AKT INHIBITOR COMPOUND WITH AN HER3/EGFR INHIBITOR COMPOUND AND USE THEREOF IN THE TREATMENT OF A HYPERPROLIFERATIVE DISORDER

(71) Applicant: THE GENERAL HOSPITAL CORPORATION, Boston, MA (US)

(72) Inventors: Jose Baselga, New York, NY (US); Maurizio Scaltriti, New York, NY (US)

(73) Assignee: THE GENERAL HOSPITAL CORPORATION, Boston, MA (US)

( * ) Notice: Subject to any disclaimer, the term of this patent is extended or adjusted under 35 U.S.C. 154(b) by 0 days.

(21) Appl. No.: 14/649,889

(22) PCT Filed: Dec. 9, 2013

(86) PCT No.: PCT/US2013/073914
§ 371 (c)(1),
(2) Date: Jun. 4, 2015

(87) PCT Pub. No.: WO2014/089570
PCT Pub. Date: Jun. 12, 2014

(65) Prior Publication Data
US 2015/0306216 A1    Oct. 29, 2015

Related U.S. Application Data

(60) Provisional application No. 61/888,892, filed on Oct. 9, 2013, provisional application No. 61/734,796, filed on Dec. 7, 2012.

(51) Int. Cl.
| | | |
|---|---|---|
| *A61K 39/00* | (2006.01) |
| *A61K 39/395* | (2006.01) |
| *A61K 31/517* | (2006.01) |
| *C07K 16/28* | (2006.01) |
| *C07K 16/32* | (2006.01) |
| *A61K 31/5377* | (2006.01) |
| *A61J 1/00* | (2006.01) |
| *G01N 33/574* | (2006.01) |

(52) U.S. Cl.
CPC ............. *A61K 39/3955* (2013.01); *A61J 1/00* (2013.01); *A61K 31/517* (2013.01); *A61K 31/5377* (2013.01); *C07K 16/2863* (2013.01); *C07K 16/32* (2013.01); *G01N 33/57415* (2013.01); *A61K 2039/505* (2013.01); *A61K 2039/507* (2013.01); *G01N 2333/71* (2013.01); *G01N 2333/912* (2013.01)

(58) Field of Classification Search
None
See application file for complete search history.

(56) References Cited

U.S. PATENT DOCUMENTS

| | | | |
|---|---|---|---|
| 7,312,243 B1 * | 12/2007 | Pravda .................. | A61K 31/12 424/653 |
| 7,781,433 B2 | 8/2010 | Chuckowree et al. | |
| 8,247,397 B2 | 8/2012 | Belvin et al. | |

FOREIGN PATENT DOCUMENTS

| | | | |
|---|---|---|---|
| WO | 2008/006040 | * | 1/2008 |
| WO | 2009/036082 | * | 3/2009 |
| WO | 2010/108127 | * | 9/2010 |
| WO | 2011112953 A2 | | 9/2011 |
| WO | 2012/135779 | * | 10/2012 |
| WO | 2012/177925 | * | 12/2012 |
| WO | 2013/075059 | * | 5/2013 |
| WO | 2013/086031 | * | 6/2013 |

OTHER PUBLICATIONS

Tao et al Cancer Research, vol. 72, (24,Suppl) .Abstract No. S5-7, 2012.*
Blake et al J. Med. Chem. vol. 55 p. 8110 (Aug. 30, 2012).*
Huang et al Cancer Research 73(2) p. 824 (2013).*
Juric et al Cancer Research, (Apr. 15, 2012) vol. 72, No. 8, Supp. 1. Abstract No. CT-08.*
Chandarlapaty et al European Journal of Cancer, (Nov. 2012) vol. 48, No. Suppl. 6, pp. 127 Abstract 417.*
Folkes et al J. Med. Chem vol. 51 p. 5522 (2008).*
Friedman et al European J. of Cancer, Supplement, vol. 8(7) p. 51, (2010), Abstract No. 142.*
Yao et al Clin. Cancer Res. vol. 15(12) p. 4147 (2009).*
Cohen, "Protein kinases—the major drug targets of the twenty-first century?", Nat Rev Drug Discov. 1 (4), 309-315 (2002).
Markman, et al., "Status of PI3K inhibition and biomarker development in cancer therapeutics", Annals of Oncology 21, 683-691 (2010).
Patent Cooperation Treaty, International Searching Authority, Search Report and Written Opinion for PCT/US2013/073914, 16 pages, Feb. 24, 2014.
Schaefer, et al., "A Two-in-One Antibody against HER3 and EGFR has Superior Inhibitory Activity Compared with Monospecific Antibodies", Cancer Cell vol. 20 (4), 472-486 (2011).
Tao, et al., "Antagonism of EGFR and HER3 Enhances the Response to Inhibitors of the PI3K-Akt Pathway in Triple-Negative Breast Cancer", Science Signaling, vol. 7, (318), ra29 1-9 (2014), Supplementary Materials 19 pages.
Teemu, et al., "Ligand-Independent HER2/HER3/PI3K Complex is Disrupted by Trastuzumab and is Effectively Inhibited by the PI3K Inhibitor GDC-0941", Cancer Cell vol. 15 (5), 429-440 (2009).
Wu, et al., "144 Reduced expression of HER3 with a specific RNA antagonist is associated with antitumor effects in preclinical models of cancer", European Journal of Cancer, vol. 8 (7), 51-52 (2010).

* cited by examiner

*Primary Examiner* — Sheela J Huff
(74) *Attorney, Agent, or Firm* — Viksnins Harris & Padys PLLP

(57) ABSTRACT

The invention provides combinations comprising GDC-0068 or GDC-0941, or a pharmaceutically acceptable salt thereof and ME-HD7945A. The combinations are particularly useful for treating hyperproliferative disorders, such as cancer (e.g., triple negative breast cancer).

8 Claims, 5 Drawing Sheets

Fig. 3
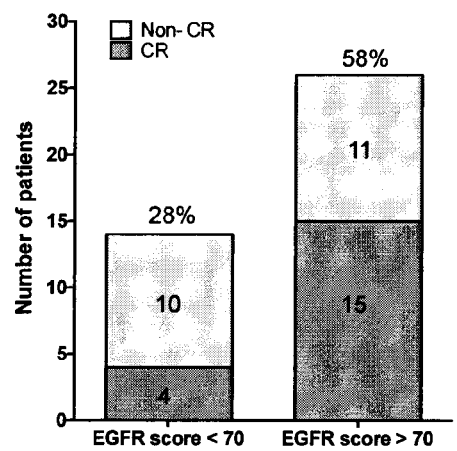
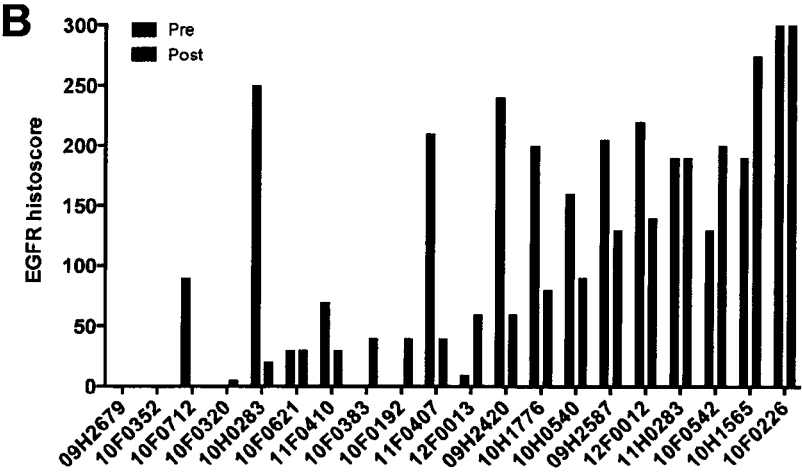
EGFR
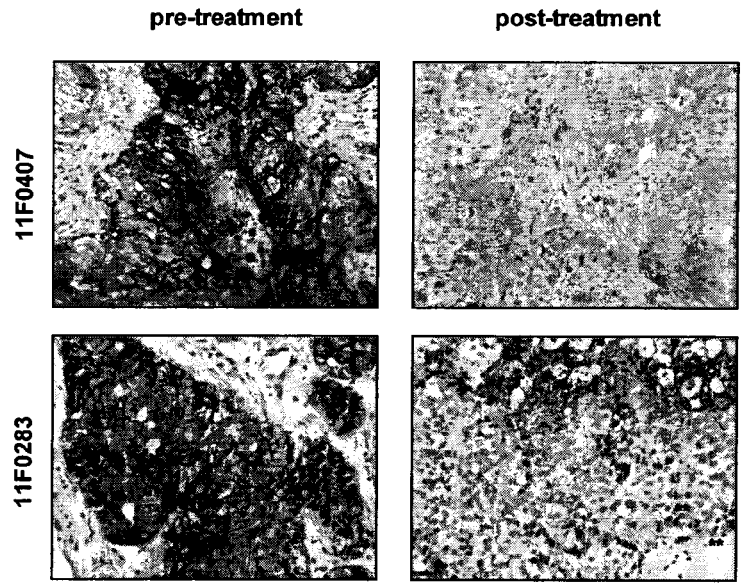

Fig. 4
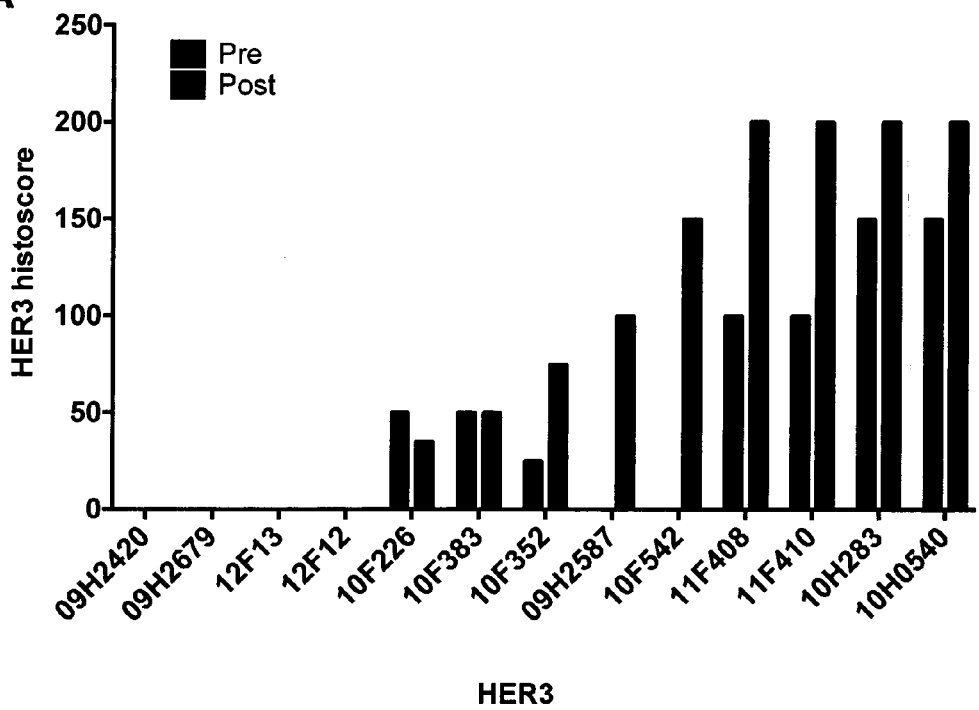
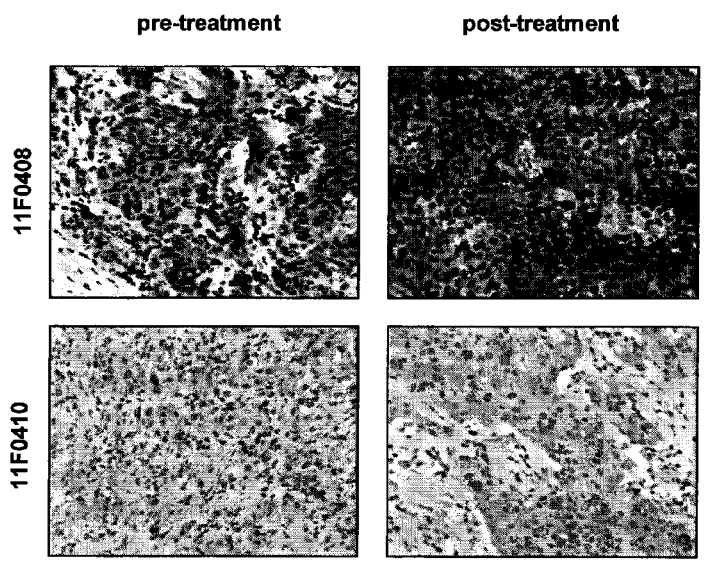

- Bivalent antibody
  - Affinity-matured human IgG1
  - Mediates ADCC
- Dual binding specificity
  - Blocks ligand-binding to HER3 and EGFR
    - $K_d$ (hu HER3) = 0.39 nM
    - $K_d$ (hu EGFR) = 1.90 nM

SEQUENCE LISTING

```
<160> NUMBER OF SEQ ID NOS: 4

<210> SEQ ID NO 1
<211> LENGTH: 121
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 1

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Leu Ser Gly Asp
            20                  25                  30

Trp Ile His Trp Val Arg Gln Ala Pro Gly Lys Gly Leu Glu Trp Val
        35                  40                  45

Gly Glu Ile Ser Ala Ala Gly Gly Tyr Thr Asp Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Glu Ser Arg Val Ser Phe Glu Ala Ala Met Asp Tyr Trp Gly
            100                 105                 110

Gln Gly Thr Leu Val Thr Val Ser Ser
        115                 120

<210> SEQ ID NO 2
<211> LENGTH: 108
<212> TYPE: PRT
<213> ORGANISM: Artificial Sequence
<220> FEATURE:
<221> NAME/KEY: source
```

<223> OTHER INFORMATION: /note="Description of Artificial Sequence:
    Synthetic polypeptide"

<400> SEQUENCE: 2

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asn Ile Ala Thr Asp
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Glu Pro Glu Pro Tyr
                85                  90                  95

Thr Phe Gly Gln Gly Thr Lys Val Glu Ile Lys Arg
            100                 105
```

<210> SEQ ID NO 3
<211> LENGTH: 451
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic polypeptide"

<400> SEQUENCE: 3

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Leu Ser Gly Asp
            20                  25                  30

Trp Ile His Trp Val Arg Gln Ala Pro Gly Lys Gly Leu Glu Trp Val
        35                  40                  45

Gly Glu Ile Ser Ala Ala Gly Gly Tyr Thr Asp Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Glu Ser Arg Val Ser Phe Glu Ala Ala Met Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220
```

```
Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450

<210> SEQ ID NO 4
<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 4

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asn Ile Ala Thr Asp
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Glu Pro Glu Pro Tyr
                85                  90                  95

Thr Phe Gly Gln Gly Thr Lys Val Glu Ile Lys Arg Thr Val Ala Ala
            100                 105                 110
```

```
-continued

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

COMBINATIONS OF A PI3K/AKT INHIBITOR COMPOUND WITH AN HER3/EGFR INHIBITOR COMPOUND AND USE THEREOF IN THE TREATMENT OF A HYPERPROLIFERATIVE DISORDER

CROSS-REFERENCE TO RELATED APPLICATION(S)

This patent application claims the benefit of priority of U.S. application Ser. No. 61/734,796, filed Dec. 7, 2012 and of U.S. application Ser. No. 61/888,892, filed Oct. 9, 2013, which applications are herein incorporated by reference.

SEQUENCE LISTING

The instant application contains a Sequence Listing which has been submitted electronically in ASCII format and is hereby incorporated by reference in its entirety. Said ASCII copy, created on Dec. 5, 2013, is named 01000.056WO1_SL.txt and is 8,675 bytes in size.

FIELD OF THE INVENTION

The invention relates generally to pharmaceutical combinations of compounds with activity against hyperproliferative disorders such as cancer (e.g., triple negative breast cancer) that include a combination of a compound that inhibits the PI3K/AKT pathway with a compound that blocks HER3/EGFR. The invention also relates to methods of using the combinations for in vitro, in situ, and in vivo diagnosis or treatment of mammalian cells, or associated pathological conditions.

BACKGROUND OF THE INVENTION

Protein kinases (PK) are enzymes that catalyze the phosphorylation of hydroxy groups on tyrosine, serine and threonine residues of proteins by transfer of the terminal (gamma) phosphate from ATP. Through signal transduction pathways, these enzymes modulate cell growth, differentiation and proliferation, i.e., virtually all aspects of cell life in one way or another depend on PK activity (Hardie, G. and Hanks, S. (1995) *The Protein Kinase Facts Book I and II*, Academic Press, San Diego, Calif.). Furthermore, abnormal PK activity has been related to a host of disorders, ranging from relatively non-life threatening diseases such as psoriasis to extremely virulent diseases such as glioblastoma (brain cancer). Protein kinases are an important target class for therapeutic modulation (Cohen, P. (2002) Nature Rev. Drug Discovery 1:309).

Currently, there remains a need for improved methods and compositions that can be used to treat hyperproliferative diseases such as cancer, e.g., triple negative breast cancer.

SUMMARY OF THE INVENTION

It has been determined that improved effects in inhibiting the growth of cancer cells in vitro and in vivo can be achieved by administering a combination of GDC-0068 or GDC-0941, or a pharmaceutically acceptable salt thereof and MEHD7945A, for the therapeutic treatment of a hyperproliferative disorder. The combinations and methods will be useful in the treatment of hyperproliferative disorders such as cancer, e.g., triple negative breast cancer. In certain embodiments, administration of the combinations may provide synergistic effects.

Accordingly, certain embodiments of the invention provide therapeutic combinations comprising the small-molecule ATP-competitive AKT inhibitor GDC-0068 (Formula I), or a pharmaceutically acceptable salt thereof (see WO 2008/006040)

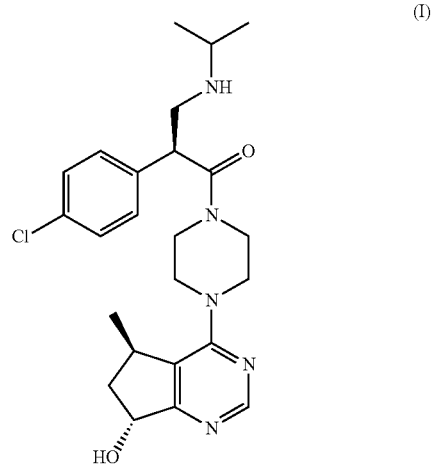 [SMILES: CC(C)NC[C@@H](C(=O)N1CCN(c2ncnc3c2[C@H](C)C[C@H]3O)CC1)c1ccc(Cl)cc1]

(I)

or the small-molecule ATP-competitive pan-PI3K inhibitor GDC-0941 (Formula II), or a pharmaceutically acceptable salt thereof (see U.S. Pat. No. 7,781,433; U.S. Pat. No. 8,247,397, Folkes et al., J. Med. Chem., 51, 5522-5532 (2008)), also known as pictilisib, CAS Registry Number: 957054-30-7, named as 4-(2-(1H-indazol-4-yl)-6-((4-(methylsulfonyl)piperazin-1-yl)methyl)thieno[3,2-d]pyrimidin-4-yl)morpholine, and having the structure:

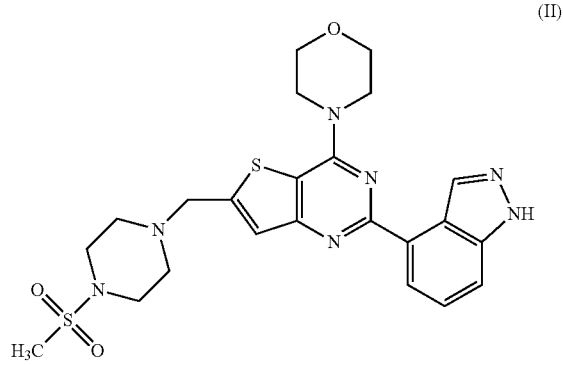 [SMILES: CS(=O)(=O)N1CCN(Cc2cc3nc(-c4cccc5[nH]ncc45)nc(N4CCOCC4)c3s2)CC1]

(II)

in combination with MEHD7945A, a dual-action antibody which comprises two identical antigen binding domains, each of which specifically binds to both HER3 and EGFR (see DL11f in WO 2010/108127 (e.g., FIG. 33) and Schaefer et al., Cancer Cell, 20, 472-486 (2011)), or in combination with ERBITUX® (cetuximab), an epidermal growth factor receptor (EGFR) antagonist currently indicated for treatment of head and neck cancer and colorectal cancer, or in combination with Vectibix® (panitumumab) an epidermal growth factor receptor antagonist currently indicated as a single agent for the treatment of metastatic colorectal carcinoma with disease progression on or following fluoropyrimidine, oxaliplatin, and irinotecan chemotherapy regimens.

Accordingly, certain embodiments of the invention are directed to a combination of GDC-0068 or GDC-0941, or a pharmaceutically acceptable salt thereof and MEHD7945A, for the therapeutic treatment of a hyperproliferative disorder.

In certain embodiments, the hyperproliferative disorder is cancer.

In certain embodiments, the cancer is associated with PTEN mutation.

In certain embodiments, the cancer is associated with AKT mutation, overexpression or amplification.

In certain embodiments, the cancer is associated with PI3K mutation.

In certain embodiments, the cancer is selected from, mesothelioma, endometrial, pancreatic, breast, lung, ovarian, prostate, melanoma, gastric, colon, renal, head and neck, and glioma.

In certain embodiments, the cancer is breast cancer.

In certain embodiments, the breast cancer is triple negative breast cancer.

In certain embodiments, GDC-0068 or a pharmaceutically acceptable salt thereof is administered in combination with MEHD7945A.

In certain embodiments, GDC-0941 or a pharmaceutically acceptable salt thereof is administered in combination with MEHD7945A.

In certain embodiments, GDC-0068 or GDC-0941, or a pharmaceutically acceptable salt thereof is administered simultaneously with MEHD7945A.

In certain embodiments, GDC-0068 or GDC-0941, or a pharmaceutically acceptable salt thereof and MEHD7945A are administered sequentially.

Certain embodiments of the invention are directed to a combination of GDC-0068 or GDC-0941, or a pharmaceutically acceptable salt thereof and MEHD7945A for therapeutic use for improving the quality of life of a patient having a hyperproliferative disorder.

Certain embodiments of the invention are directed to a combination of GDC-0068 or GDC-0941, or a pharmaceutically acceptable salt thereof; and MEHD7945A, for treating a hyperproliferative disorder.

Certain embodiments of the invention are directed to a combination of GDC-0068 or GDC-0941, or a pharmaceutically acceptable salt thereof; and MEHD7945A, for treating a disease or condition modulated by AKT kinase.

Certain embodiments of the invention are directed to a use of a combination of GDC-0068 or GDC-0941, or a pharmaceutically acceptable salt thereof; and MEHD7945A, in the preparation of a medicament for the treatment of a hyperproliferative disorder in a mammal.

Certain embodiments of the invention are directed to a use of a combination of GDC-0068 or GDC-0941, or a pharmaceutically acceptable salt thereof; and MEHD7945A, in preparation of a medicament for the treatment of a disease or condition modulated by AKT kinase in a mammal.

Certain embodiments of the invention are directed to a kit comprising GDC-0068 or GDC-0941, or a pharmaceutically acceptable salt thereof; and MEHD7945A, a container, and a package insert or label indicating the administration GDC-0068 or GDC-0941, or a pharmaceutically acceptable salt thereof; and MEHD7945A, for treating a hyperproliferative disorder (e.g., cancer, e.g., triple negative breast cancer).

Certain embodiments of the invention are directed to a product comprising GDC-0068 or GDC-0941, or a pharmaceutically acceptable salt thereof and MEHD7945A as a combined preparation for separate, simultaneous or sequential use in the treatment of a hyperproliferative disorder.

Certain embodiments of the invention are directed to a method for treating a hyperproliferative disorder in a mammal (e.g., cancer, e.g., triple negative breast cancer), comprising administering to the mammal a combination of GDC-0068 or GDC-0941, or a pharmaceutically acceptable salt thereof; and MEHD7945A.

Certain embodiments of the invention are directed to a method for treating a disease or condition modulated by AKT kinase in a mammal comprising, administering to the mammal, a combination of GDC-0068 or GDC-0941, or a pharmaceutically acceptable salt thereof; and MEHD7945A.

In certain embodiments, the mammal is a human having triple negative breast cancer (TNBC) that has been selected for treatment as having TNBC with elevated EGFR expression.

In certain embodiments, HER3 expression is measured following the treatment, wherein relatively elevated HER3 expression indicates an elevated risk for lack of complete tumor regression.

BRIEF DESCRIPTION OF THE DRAWINGS

FIG. 3. EGFR expression and response to anti-EGFR therapy in TNBC patients. (A) Correlation between baseline EGFR expression and pathological complete response (pCR) in 40 TNBC patients treated with panitumumab-based therapy. (B) Changes in EGFR expression between baseline and residual tumor of the patients who did not achieve pCR upon treatment with panitumumab-based therapy. Left bars are pre and right bars are post. (C)

Representative IHCs showing decreased EGFR expression in residual tumors (post-treatment) versus baseline specimens (pre-treatment).

FIG. 4. HER3 expression and response to anti-EGFR therapy in TNBC patients. (A) Changes in HER3 expression between baseline and residual tumor of the patients who did not achieve pCR upon treatment with panitumumab-based therapy. Left bars are pre and right bars are post. (B) Representative IHCs showing increase HER3 expression in residual tumors (post-treatment) versus baseline specimens (pre-treatment).

Figure 5:
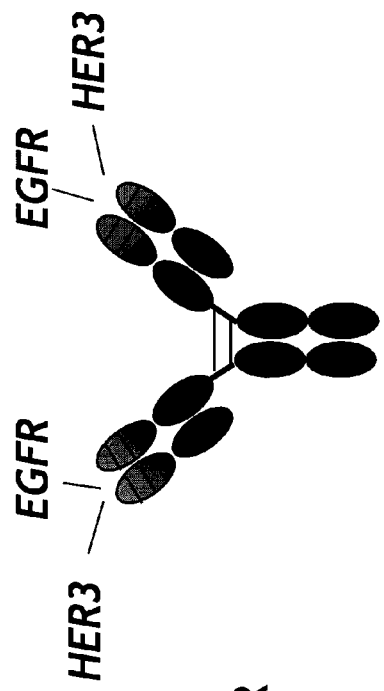

FIG. 5 depicts MEHD7945A as a dual HER3/EGFR inhibitor.

DETAILED DESCRIPTION OF EXEMPLARY EMBODIMENTS AND DEFINITIONS

The words "comprise," "comprising," "include," "including," and "includes" when used in this specification and claims are intended to specify the presence of stated features, integers, components, or steps, but they do not preclude the presence or addition of one or more other features, integers, components, steps, or groups thereof.

The terms "treat" and "treatment" refer to therapeutic treatment, wherein the object is to prevent or slow down (lessen) an undesired physiological change or disorder, such as the growth, development or spread of cancer. For purposes of this invention, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already having the condition or disorder, e.g., a patient with triple negative breast cancer.

The phrase "therapeutically effective amount" means an amount that (i) treats the particular disease, condition, or disorder, (ii) attenuates, ameliorates, or eliminates one or more symptoms of the particular disease, condition, or disorder, or (iii) prevents or delays the onset of one or more symptoms of the particular disease, condition, or disorder described herein. In the case of cancer, the therapeutically effective amount may reduce the number of cancer cells; reduce the tumor size; inhibit (e.g., slow to some extent and preferably stop) cancer cell infiltration into peripheral organs; inhibit (e.g., slow to some extent and preferably stop) tumor metastasis; inhibit, to some extent, tumor growth; and/or relieve to some extent one or more of the symptoms associated with the cancer. To the extent the combination may prevent growth and/or kill existing cancer cells, it may be cytostatic and/or cytotoxic. For cancer therapy, efficacy can be measured, for example, by assessing the time to disease progression (TTP) and/or determining the response rate (RR).

The terms "cancer" and "cancerous" refer to or describe the physiological condition in mammals that is typically characterized by unregulated cell growth. A "tumor" comprises one or more cancerous cells. Examples of cancer include, but are not limited to, carcinoma, lymphoma, blastoma, sarcoma, and leukemia or lymphoid malignancies. More particular examples of such cancers include squamous cell cancer (e.g., epithelial squamous cell cancer), lung cancer including small-cell lung cancer, non-small cell lung cancer ("NSCLC"), adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer (e.g., triple negative breast cancer), colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, as well as head and neck cancer. Gastric cancer, as used herein, includes stomach cancer, which can develop in any part of the stomach and may spread throughout the stomach and to other organs; particularly the esophagus, lungs, lymph nodes, and the liver.

A "chemotherapeutic agent" is a biological (e.g., large molecule) or chemical (e.g., small molecule) compound useful in the treatment of cancer, regardless of mechanism of action.

A "platinum agent" is a chemotherapeutic agent that comprises platinum, for example carboplatin, cisplatin, and oxaliplatin.

The term "mammal" includes, but is not limited to, humans, mice, rats, guinea pigs, monkeys, dogs, cats, horses, cows, pigs, sheep, and poultry. The term patient refers to a mammal, and in one embodiment, the patient is a human male or a human female.

The term "package insert" is used to refer to instructions customarily included in commercial packages of therapeutic products that contain information about the indications, usage, dosage, administration, contraindications and/or warnings concerning the use of such therapeutic products.

The phrase "pharmaceutically acceptable salt" as used herein, refers to pharmaceutically acceptable organic or inorganic salts of a compound. Exemplary salts include, but are not limited, to bismesylate, sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucuronate, saccharate, formate, benzoate, glutamate, methanesulfonate "mesylate", ethanesulfonate, benzenesulfonate, p-toluenesulfonate, and pamoate (i.e., 1,1'-methylene-bis-(2-hydroxy-3-naphthoate)) salts. A pharmaceutically acceptable salt may involve the inclusion of another molecule such as an acetate ion, a succinate ion or other counter ion. The counter ion may be any organic or inorganic moiety that stabilizes the charge on the parent compound. Furthermore, a pharmaceutically acceptable salt may have more than one charged atom in its structure. Instances where multiple charged atoms are part of the pharmaceutically acceptable salt can have multiple counter ions. Hence, a pharmaceutically acceptable salt can have one or more charged atoms and/or one or more counter ion.

The desired pharmaceutically acceptable salt may be prepared by any suitable method available in the art. For example, treatment of the free base with an inorganic acid, such as hydrochloric acid, hydrobromic acid, sulfuric acid, nitric acid, methanesulfonic acid, phosphoric acid and the like, or with an organic acid, such as acetic acid, maleic acid, succinic acid, mandelic acid, fumaric acid, malonic acid, pyruvic acid, oxalic acid, glycolic acid, salicylic acid, a pyranosidyl acid, such as glucuronic acid or galacturonic acid, an alpha hydroxy acid, such as citric acid or tartaric acid, an amino acid, such as aspartic acid or glutamic acid, an aromatic acid, such as benzoic acid or cinnamic acid, a sulfonic acid, such as p-toluenesulfonic acid or ethanesulfonic acid, or the like. Acids which are generally considered suitable for the formation of pharmaceutically useful or acceptable salts from basic pharmaceutical compounds are discussed, for example, by P. Stahl et al, Camille G. (eds.) Handbook of Pharmaceutical Salts. Properties, Selection and Use. (2002) Zurich: Wiley-VCH; S. Berge et al, Journal of Pharmaceutical Sciences (1977) 66(1) 1 19; P. Gould, International J. of Pharmaceutics (1986) 33 201 217; Anderson et al, The Practice of Medicinal Chemistry (1996), Academic Press, New York; Remington's Pharmaceutical Sciences, 18$^{th}$ ed., (1995) Mack Publishing Co., Easton Pa.; and in The Orange Book (Food & Drug Administration, Washington, D.C. on their website). These disclosures are incorporated herein by reference thereto.

The phrase "pharmaceutically acceptable" indicates that the substance or composition is compatible chemically and/ or toxicologically with the other ingredients comprising a formulation and/or the mammal being treated therewith.

The term "synergistic" as used herein refers to a therapeutic combination which is more effective than the additive effects of the two or more single agents. A determination of a synergistic interaction may be based on the results obtained from the assays known in the art. The results of these assays can be analyzed using the Chou and Talalay combination method and Dose-Effect Analysis with CalcuSyn software in order to obtain a Combination Index (Chou and Talalay, 1984, Adv. Enzyme Regul. 22:27-55). The combinations provided herein can be analyzed utilizing a standard program for quantifying synergism, additivism, and antagonism among anticancer agents. An example program is that described by Chou and Talalay, in "New Avenues in Developmental Cancer Chemotherapy," Academic Press, 1987, Chapter 2. Combination Index values less than 0.8 indicates synergy, values greater than 1.2 indicate antagonism and values between 0.8 to 1.2 indicate additive effects. The combination therapy may provide "synergy" and prove "synergistic", i.e., the effect achieved when the active ingredients used together is greater than the sum of the effects that results from using the compounds separately. A synergistic effect may be attained when the active ingredients are: (1) co-formulated and administered or delivered simultaneously in a combined, unit dosage formulation; (2) delivered by alternation or in parallel as separate formulations; or (3) by some other regimen. When delivered in alternation therapy, a synergistic effect may be attained when the compounds are administered or delivered sequentially, e.g., by different injections in separate syringes. In general, during alternation therapy, an effective dosage of each active ingredient is administered sequentially, i.e., serially, whereas in combination therapy, effective dosages of two or more active ingredients are administered together. Combination effects were evaluated using both the BLISS independence model and the highest single agent (HSA) model (Lehár et al. 2007, Molecular Systems Biology 3:80). BLISS scores quantify degree of potentiation from single agents and a positive BLISS score (greater than 0) suggests greater than simple additivity. A cumulative positive BLISS score greater than 250 is considered strong synergy observed within the concentration ranges tested. An HSA score (greater than 0) suggests a combination effect greater than the maximum of the single agent responses at corresponding concentrations. The mutation status of the cancer cell may be a biomarker of how the cancer cell will respond to different treatment protocols. For example, cancer cells that have PI3K pathway (e.g. PI3K or AKT) mutations may display positive (e.g., synergistic) responses to the combination treatments described herein. Further, the PTEN status of the cancer cell may also be a biomarker. Accordingly, certain embodiments of the invention include methods of treating cancer cells (in vitro or in vivo) that have combinations of these biomarkers with these combination treatments. Certain embodiments of the invention include selecting patients for combination treatment that have combinations of these biomarkers.

In addition to providing improved treatment for a given hyperproliferative disorder, administration of certain combinations of the invention may improve the quality of life for a patient compared to the quality of life experienced by the same patient receiving a different treatment. For example, administration of a combination to a patient may provide an improved quality of life compared to the quality of life the same patient would experience if they received only one of the individual agents as therapy. For example, the combined therapy with a combination described herein may lower the dose of therapeutic agents needed. The combination therapy may also decrease or eliminate the need for the use of chemotherapeutic agents and the side-effects associated with high-dose chemotherapeutic agents (e.g. nausea, vomiting, hair loss, rash, decreased appetite, weight loss, etc.). The combination may also cause reduced tumor burden and the associated adverse events, such as pain, organ dysfunction, weight loss, etc. Accordingly, one aspect of the invention provides a combination for therapeutic use for improving the quality of life of a patient treated for a hyperproliferative disorder with a combination described herein.

One aspect includes a method of tumor growth inhibition (TGI) in a patient suffering from a cancer, e.g., comprising a PI3K, AKT or PTEN mutation, comprising administering a combination described herein to the patient. In certain embodiments, the combination provides a synergistic effect.

In certain embodiments, the TGI of the combination is greater than the TGI of any one of GDC-0068 or GDC-0941 or MEHD7945A alone. In certain embodiments, the TGI of the combination is about 10, 15, 20, 25, 30, 35, 40, 45, 50, 55, 60, 65, 70 or 75 percent greater than the TGI of the agents alone.

Methods of measuring TGI are known in the art. In one example method, average tumor volumes are determined and compared from the patient before and after treatment. Tumor volumes can be measured in two dimensions (length and width) using any method in the art, for example UltraCal IV calipers (Fred V. Fowler Company) or by PET (positron emission tomography), or by some other method. The formula tumor volume $(mm^3)=(length \times width^2) \times 0.5$ can be used. Measuring tumor volumes over multiple time periods can be done using a mixed-modeling Linear Mixed Effects (LME) approach (Pinheiro et al. 2009). This approach can address both repeated measurements (and multiple patients). Cubic regression splines can be used to fit a non-linear profile to the time courses of tumor volume at each dose level. These non-linear profiles can then be related to dose within the mixed model. Tumor growth inhibition as a percent of vehicle can be calculated as a percent area under the fitted curve (AUC) per day in relation to the vehicle, using the following formula:

$$\% \, TGI = 100 \left[ 1 - \left( \frac{AUC_{treatment}/day}{AUC_{vehicle}/day} \right) \right]$$

Using this formula, a TGI value of 100% indicates tumor stasis, greater than about 1% but less than about 100% indicates tumor growth inhibition, and greater than about 100% indicates tumor regression.

Preparation of GDC-0068, GDC-0941 and MEHD7945a

The small-molecule ATP-competitive AKT inhibitor GDC-0068 (Formula I), or a pharmaceutically acceptable salt thereof can be prepared e.g., as described in WO 2008/006040:

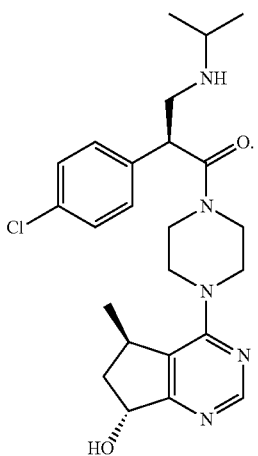

(I)

The small-molecule ATP-competitive pan-PI3K inhibitor GDC-0941 (Formula II), or a pharmaceutically acceptable salt thereof can be prepared, e.g., as described in U.S. Pat. No. 7,781,433, US 2010/0292468, or Folkes et al., J. Med. Chem., 51, 5522-5532 (2008):

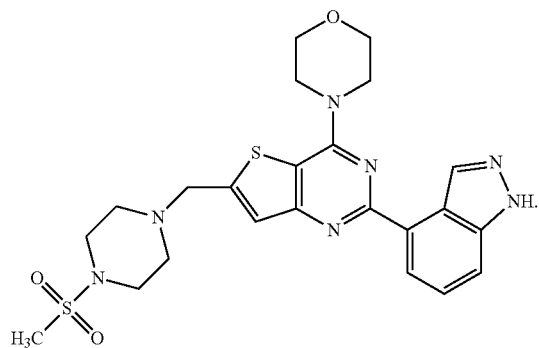

(II)

The dual-action antibody MEHD7945A which comprises two identical antigen binding domains, each of which specifically binds to both HERS and EGFR can be prepared as described in WO 2010/108127 (see DL11f, e.g., FIG. 33) and Schaefer et al., Cancer Cell, 20, 472-486 (2011). The amino acid sequence of MEHD7945A for the heavy chain variable domain is provided as SEQ ID NO: 1 and the light chain variable domain as SEQ ID NO: 2. The amino acid sequence of MEHD7945A for the heavy chain domain is provided as SEQ ID NO: 3 and the light chain variable domain as SEQ ID NO: 4.

Methods of Separation

In any of the synthetic methods for preparing compounds, it may be advantageous to separate reaction products from one another and/or from starting materials. The desired products of each step or series of steps is separated and/or purified to the desired degree of homogeneity by the techniques common in the art. Typically such separations involve multiphase extraction, crystallization from a solvent or solvent mixture, distillation, sublimation, or chromatography. Chromatography can involve any number of methods including, for example: reverse-phase and normal phase; size exclusion; ion exchange; high, medium and low pressure liquid chromatography methods and apparatus; small scale analytical; simulated moving bed (SMB) and preparative thin or thick layer chromatography, as well as techniques of small scale thin layer and flash chromatography.

Another class of separation methods involves treatment of a reaction mixture with a reagent selected to bind to or render otherwise separable a desired product, unreacted starting material, reaction by product, or the like. Such reagents include adsorbents or absorbents such as activated carbon, molecular sieves, ion exchange media, or the like. Alternatively, the reagents can be acids in the case of a basic material, bases in the case of an acidic material, binding reagents such as antibodies, binding proteins, selective chelators such as crown ethers, liquid/liquid ion extraction reagents (LIX), or the like.

Selection of appropriate methods of separation depends on the nature of the materials involved. For example, boiling point and molecular weight in distillation and sublimation, presence or absence of polar functional groups in chromatography, stability of materials in acidic and basic media in multiphase extraction, and the like. One skilled in the art will apply techniques most likely to achieve the desired separation.

Diastereomeric mixtures can be separated into their individual diastereomers on the basis of their physical chemical differences by methods well known to those skilled in the art, such as by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereoisomers to the corresponding pure enantiomers. Also, some of the compounds of the present invention may be atropisomers (e.g., substituted biaryls) and are considered as part of this invention. Enantiomers can also be separated by use of a chiral HPLC column.

A single stereoisomer, e.g., an enantiomer, substantially free of its stereoisomer may be obtained by resolution of the racemic mixture using a method such as formation of diastereomers using optically active resolving agents (Eliel, E. and Wilen, S. "Stereochemistry of Organic Compounds," John Wiley & Sons, Inc., New York, 1994; Lochmuller, C. H., J. Chromatogr., (1975) 113(3):283-302). Racemic mixtures of chiral compounds of the invention can be separated and isolated by any suitable method, including: (1) formation of ionic, diastereomeric salts with chiral compounds and separation by fractional crystallization or other methods, (2) formation of diastereomeric compounds with chiral derivatizing reagents, separation of the diastereomers, and conversion to the pure stereoisomers, and (3) separation of the substantially pure or enriched stereoisomers directly under chiral conditions. See: "Drug Stereochemistry, Analytical Methods and Pharmacology," Irving W. Wainer, Ed., Marcel Dekker, Inc., New York (1993). Under method (1), diastereomeric salts can be formed by reaction of enantiomerically pure chiral bases such as brucine, quinine, ephedrine, strychnine, α-methyl-β-phenylethylamine(amphetamine), and the like with asymmetric compounds bearing acidic functionality, such as carboxylic acid and sulfonic acid. The diastereomeric salts may be induced to separate by fractional crystallization or ionic chromatography. For separation of the optical isomers of amino compounds, addition of chiral carboxylic or sulfonic acids, such as camphorsulfonic acid, tartaric acid, mandelic acid, or lactic acid can result in formation of the diastereomeric salts.

Alternatively, by method (2), the substrate to be resolved is reacted with one enantiomer of a chiral compound to form a diastereomeric pair (E. and Wilen, S. "Stereochemistry of Organic Compounds", John Wiley & Sons, Inc., 1994, p. 322). Diastereomeric compounds can be formed by reacting asymmetric compounds with enantiomerically pure chiral derivatizing reagents, such as menthyl derivatives, followed by separation of the diastereomers and hydrolysis to yield the pure or enriched enantiomer. A method of determining optical purity involves making chiral esters, such as a menthyl ester, e.g., (−)menthyl chloroformate in the presence of base, or Mosher ester, α-methoxy-α-(trifluoromethyl)phenyl acetate (Jacob III. *J. Org. Chem.*, (1982) 47:4165), of the racemic mixture, and analyzing the $^1$H NMR spectrum for the presence of the two atropisomeric enantiomers or diastereomers. Stable diastereomers of atropisomeric compounds can be separated and isolated by normal- and reverse-phase chromatography following methods for separation of atropisomeric naphthyl-isoquinolines (WO 96/15111). By method (3), a racemic mixture of two enantiomers can be separated by chromatography using a chiral stationary phase ("Chiral Liquid Chromatography" (1989) W. J. Lough, Ed., Chapman and Hall, New York; Okamoto, *J. of Chromatogr.*, (1990) 513:375-378). Enriched or purified enantiomers can be distinguished by methods used to distinguish other chiral molecules with asymmetric carbon atoms, such as optical rotation and circular dichroism.

Pharmaceutical Compositions

Pharmaceutical compositions or formulations of the present invention include combinations as described herein.

The compounds described herein or a pharmaceutically acceptable salt thereof may exist in unsolvated as well as solvated forms with pharmaceutically acceptable solvents such as water, ethanol, and the like, and it is intended that the invention embrace both solvated and unsolvated forms.

The compound or a pharmaceutically acceptable salt thereof may also exist in different tautomeric forms, and all such forms are embraced within the scope of the invention. The term "tautomer" or "tautomeric form" refers to structural isomers of different energies which are interconvertible via a low energy barrier. For example, proton tautomers (also known as prototropic tautomers) include interconversions via migration of a proton, such as keto-enol and imine-enamine isomerizations. Valence tautomers include interconversions by reorganization of some of the bonding electrons.

Pharmaceutical compositions encompass both the bulk composition and individual dosage units comprised of more than one (e.g., two) pharmaceutically active agents, along with any pharmaceutically inactive excipients, diluents, carriers, or glidants. The bulk composition and each individual dosage unit can contain fixed amounts of the aforesaid pharmaceutically active agents. The bulk composition is material that has not yet been formed into individual dosage units. An illustrative dosage unit is an oral dosage unit such as tablets, pills, capsules, and the like. Similarly, the herein-described method of treating a patient by administering a pharmaceutical composition of the present invention is also intended to encompass the administration of the bulk composition and individual dosage units.

Pharmaceutical compositions also embrace isotopically-labeled compounds which are identical to those recited herein, but for the fact that one or more atoms are replaced by an atom having an atomic mass or mass number different from the atomic mass or mass number usually found in nature. All isotopes of any particular atom or element as specified are contemplated within the scope of the compounds of the invention, and their uses. Exemplary isotopes that can be incorporated into compounds include isotopes of hydrogen, carbon, nitrogen, oxygen, phosphorus, sulfur, fluorine, chlorine and iodine, such as $^2$H, $^3$H, $^{11}$C, $^{13}$C, $^{14}$C, $^{13}$N, $^{15}$N, $^{15}$O, $^{17}$O, $^{18}$O, $^{32}$P, $^{33}$P, $^{35}$S, $^{18}$F, $^{36}$Cl, $^{123}$I and $^{125}$I. Certain isotopically-labeled compounds of the present invention (e.g., those labeled with $^3$H and $^{14}$C) are useful in compound and/or substrate tissue distribution assays. Tritiated ($^3$H) and carbon-14 ($^{14}$C) isotopes are useful for their ease of preparation and detectability. Further, substitution with heavier isotopes such as deuterium ($^2$H) may afford certain therapeutic advantages resulting from greater metabolic stability (e.g., increased in vivo half-life or reduced dosage requirements) and hence may be preferred in some circumstances. Positron emitting isotopes such as $^{15}$O, $^{13}$N, $^{11}$C and $^{18}$F are useful for positron emission tomography (PET) studies to examine substrate receptor occupancy.

The pharmaceutically acceptable salts of the compounds are formulated in accordance with standard pharmaceutical practice for use in a therapeutic combination for therapeutic treatment of hyperproliferative disorders (such as cancer, such as triple negative breast cancer) in mammals including humans (such as human males or females). The invention provides a pharmaceutical composition comprising a combination as described herein in association with one or more pharmaceutically acceptable carrier, glidant, diluent, or excipient.

Suitable carriers, diluents and excipients are well known to those skilled in the art and include materials such as carbohydrates, waxes, water soluble and/or swellable polymers, hydrophilic or hydrophobic materials, gelatin, oils, solvents, water and the like. The particular carrier, diluent or excipient used will depend upon the means and purpose for which the compound of the present invention is being applied. Solvents are generally selected based on solvents recognized by persons skilled in the art as safe (GRAS) to be administered to a mammal. In general, safe solvents are non-toxic aqueous solvents such as water and other non-toxic solvents that are soluble or miscible in water. Suitable aqueous solvents include water, ethanol, propylene glycol, polyethylene glycols (e.g., PEG 400, PEG 300), etc. and mixtures thereof. The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents and other known additives to provide an elegant presentation of the drug (i.e., a compound of the present invention or pharmaceutical composition thereof) or aid in the manufacturing of the pharmaceutical product (i.e., medicament).

The formulations may be prepared using conventional dissolution and mixing procedures. For example, the bulk drug substance (i.e., compound of the present invention or stabilized form of the compound (e.g., complex with a cyclodextrin derivative or other known complexation agent) is dissolved in a suitable solvent in the presence of one or more of the excipients described above. The compound of the present invention is typically formulated into pharmaceutical dosage forms to provide an easily controllable dosage of the drug and to enable patient compliance with the prescribed regimen.

The pharmaceutical composition (or formulation) for administration may be packaged in a variety of ways depending upon the method used for administering the drug. Generally, an article for distribution includes a container having deposited therein the pharmaceutical formulation in an appropriate form. Suitable containers are well known to those skilled in the art and include materials such as bottles (plastic and glass), sachets, ampoules, plastic bags, metal cylinders, and the like. The container may also include a tamper-proof assemblage to prevent indiscreet access to the contents of the package. In addition, the container has deposited thereon a label that describes the contents of the container. The label may also include appropriate warnings.

Pharmaceutical formulations of the compounds may be prepared for various routes and types of administration. For example, the compound or a pharmaceutically acceptable salt thereof having the desired degree of purity may optionally be mixed with pharmaceutically acceptable diluents, carriers, excipients or stabilizers (Remington's Pharmaceutical Sciences (1995) 18th edition, Mack Publ. Co., Easton, Pa.), in the form of a lyophilized formulation, milled powder, or an aqueous solution. Formulation may be conducted by mixing at ambient temperature at the appropriate pH, and at the desired degree of purity, with physiologically acceptable carriers, i.e., carriers that are non-toxic to recipients at the dosages and concentrations employed. The pH of the formulation depends mainly on the particular use and the concentration of compound, but may range from about 3 to about 8.

The pharmaceutical formulation is preferably sterile. In particular, formulations to be used for in vivo administration must be sterile. Such sterilization is readily accomplished by filtration through sterile filtration membranes.

The pharmaceutical formulation ordinarily can be stored as a solid composition, a lyophilized formulation or as an aqueous solution.

The pharmaceutical formulations will be dosed and administered in a fashion, e.g., amounts, concentrations, schedules, course, vehicles and route of administration, consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The "therapeutically effective amount" to be administered will be governed by such considerations, and is the minimum amount necessary to prevent, ameliorate, or treat the disorder. Such amount is preferably below the amount that is toxic to the host or renders the host significantly more susceptible to bleeding.

Acceptable diluents, carriers, excipients and stabilizers are nontoxic to recipients at the dosages and concentrations employed, and include buffers such as phosphate, citrate and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG). The active pharmaceutical ingredients may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in Remington's Pharmaceutical Sciences 18th edition, (1995) Mack Publ. Co., Easton, Pa.

Sustained-release preparations may be prepared. Suitable examples of sustained-release preparations include semipermeable matrices of solid hydrophobic polymers containing a compound or a pharmaceutically acceptable salt thereof, which matrices are in the form of shaped articles, e.g., films, or microcapsules. Examples of sustained-release matrices include polyesters, hydrogels (for example, poly(2-hydroxyethyl-methacrylate), or poly(vinyl alcohol)), polylactides (U.S. Pat. No. 3,773,919), copolymers of L-glutamic acid and gamma-ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate) and poly-D(-)3-hydroxybutyric acid.

The pharmaceutical formulations include those suitable for the administration routes detailed herein. The formulations may conveniently be presented in unit dosage form and may be prepared by any of the methods well known in the art of pharmacy. Techniques and formulations generally are found in Remington's Pharmaceutical Sciences $18^{th}$ Ed. (1995) Mack Publishing Co., Easton, Pa. Such methods include the step of bringing into association the active ingredient with the carrier which constitutes one or more accessory ingredients. In general the formulations are prepared by uniformly and intimately bringing into association the active ingredient with liquid carriers or finely divided solid carriers or both, and then, if necessary, shaping the product.

Formulations of combinations suitable for oral administration may be prepared as discrete units such as pills, hard or soft e.g., gelatin capsules, cachets, troches, lozenges, aqueous or oil suspensions, dispersible powders or granules, emulsions, syrups or elixirs each containing a predetermined amount of GDC-0068 or GDC-0941, or a pharmaceutically acceptable salt thereof; and MEHD7945A. The amount of GDC-0068 or GDC-0941, or a pharmaceutically acceptable salt thereof; and MEHD7945A may be formulated in a pill, capsule, solution or suspension as a combined formulation. Alternatively, the combination may be formulated separately in a pill, capsule, solution or suspension for administration by alternation.

Formulations may be prepared according to any method known to the art for the manufacture of pharmaceutical compositions and such compositions may contain one or more agents including sweetening agents, flavoring agents, coloring agents and preserving agents, in order to provide a palatable preparation. Compressed tablets may be prepared by compressing in a suitable machine the active ingredient in a free-flowing form such as a powder or granules, optionally mixed with a binder, lubricant, inert diluent, preservative, surface active or dispersing agent. Molded tablets may be made by molding in a suitable machine a mixture of the powdered active ingredient moistened with an inert liquid diluent.

The tablets may optionally be coated or scored and optionally are formulated so as to provide slow or controlled release of the active ingredient therefrom. Tablet excipients of a pharmaceutical formulation may include: Filler (or diluent) to increase the bulk volume of the powdered drug making up the tablet; Disintegrants to encourage the tablet to break down into small fragments, ideally individual drug particles, when it is ingested and promote the rapid dissolution and absorption of drug; Binder to ensure that granules and tablets can be formed with the required mechanical strength and hold a tablet together after it has been compressed, preventing it from breaking down into its component powders during packaging, shipping and routine handling; Glidant to improve the flowability of the powder making up the tablet during production; Lubricant to ensure that the tableting powder does not adhere to the equipment used to press the tablet during manufacture. They improve the flow of the powder mixes through the presses and minimize friction and breakage as the finished tablets are ejected from the equipment; Antiadherent with function similar to that of the glidant, reducing adhesion between the powder making up the tablet and the machine that is used to punch out the shape of the tablet during manufacture; Flavor incorporated into tablets to give them a more pleasant taste or to mask an unpleasant one, and Colorant to aid identification and patient compliance.

Tablets containing the active ingredient in admixture with non-toxic pharmaceutically acceptable excipient which are suitable for manufacture of tablets are acceptable. These excipients may be, for example, inert diluents, such as calcium or sodium carbonate, lactose, calcium or sodium phosphate; granulating and disintegrating agents, such as maize starch, or alginic acid; binding agents, such as starch, gelatin or acacia; and lubricating agents, such as magnesium stearate, stearic acid or talc. Tablets may be uncoated or may be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax may be employed.

For treatment of the eye or other external tissues, e.g., mouth and skin, the formulations are preferably applied as a topical ointment or cream containing the active ingredient(s) in an amount of, for example, 0.075 to 20% w/w. When formulated in an ointment, the active ingredients may be employed with either a paraffinic or a water-miscible ointment base. Alternatively, the active ingredients may be formulated in a cream with an oil-in-water cream base.

If desired, the aqueous phase of the cream base may include a polyhydric alcohol, i.e., an alcohol having two or more hydroxyl groups such as propylene glycol, butane 1,3-diol, mannitol, sorbitol, glycerol and polyethylene glycol (including PEG 400) and mixtures thereof. The topical formulations may desirably include a compound which enhances absorption or penetration of the active ingredient through the skin or other affected areas. Examples of such dermal penetration enhancers include dimethyl sulfoxide and related analogs.

The oily phase of the emulsions of this invention may be constituted from known ingredients in a known manner, including a mixture of at least one emulsifier with a fat or an oil, or with both a fat and an oil. Preferably, a hydrophilic emulsifier is included together with a lipophilic emulsifier which acts as a stabilizer. Together, the emulsifier(s) with or without stabilizer(s) make up an emulsifying wax, and the wax together with the oil and fat comprise an emulsifying ointment base which forms the oily dispersed phase of cream formulations. Emulsifiers and emulsion stabilizers suitable for use in the formulation include Tween® 60, Span® 80, cetostearyl alcohol, benzyl alcohol, myristyl alcohol, glyceryl monostearate and sodium lauryl sulfate.

Aqueous suspensions of the pharmaceutical formulations contain the active materials in admixture with excipients suitable for the manufacture of aqueous suspensions. Such excipients include a suspending agent, such as sodium carboxymethylcellulose, croscarmellose, povidone, methylcellulose, hydroxypropyl methylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycetanol), a condensation product of ethylene oxide with a partial ester derived from a fatty acid and a hexitol anhydride (e.g., polyoxyethylene sorbitan monooleate). The aqueous suspension may also contain one or more preservatives such as ethyl or n-propyl p-hydroxybenzoate, one or more coloring agents, one or more flavoring agents and one or more sweetening agents, such as sucrose or saccharin.

Pharmaceutical compositions may be in the form of a sterile injectable preparation, such as a sterile injectable aqueous or oleaginous suspension. This suspension may be formulated according to the known art using those suitable dispersing or wetting agents and suspending agents which have been mentioned above. The sterile injectable preparation may be a solution or a suspension in a non-toxic parenterally acceptable diluent or solvent, such as a solution in 1,3-butanediol or prepared from a lyophilized powder. Among the acceptable vehicles and solvents that may be employed are water, Ringer's solution and isotonic sodium chloride solution. In addition, sterile fixed oils may conventionally be employed as a solvent or suspending medium. For this purpose any bland fixed oil may be employed including synthetic mono- or diglycerides. In addition, fatty acids such as oleic acid may likewise be used in the preparation of injectables.

The amount(s) of active ingredient(s) that may be combined with the carrier material to produce a single dosage form will vary depending upon the host treated and the particular mode of administration. For example, a time-release formulation intended for oral administration to humans may contain approximately 1 to 1000 mg of active material compounded with an appropriate and convenient amount of carrier material which may vary from about 5 to about 95% of the total compositions (weight:weight). The pharmaceutical composition can be prepared to provide easily measurable amounts for administration. For example, an aqueous solution intended for intravenous infusion may contain from about 3 to 500 μg of the active ingredient per milliliter of solution in order that infusion of a suitable volume at a rate of about 30 mL/hr can occur.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents.

Formulations suitable for topical administration to the eye also include eye drops wherein the active ingredient is dissolved or suspended in a suitable carrier, especially an aqueous solvent for the active ingredient. The active ingredient is preferably present in such formulations in a concentration of about 0.5 to 20% w/w, for example about 0.5 to 10% w/w, for example about 1.5% w/w.

Formulations suitable for topical administration in the mouth include lozenges comprising the active ingredient in a flavored basis, usually sucrose and acacia or tragacanth; pastilles comprising the active ingredient in an inert basis such as gelatin and glycerin, or sucrose and acacia; and mouthwashes comprising the active ingredient in a suitable liquid carrier.

Formulations for rectal administration may be presented as a suppository with a suitable base comprising for example cocoa butter or a salicylate.

Formulations suitable for intrapulmonary or nasal administration have a particle size for example in the range of 0.1 to 500 microns (including particle sizes in a range between 0.1 and 500 microns in increments microns such as 0.5, 1, 30 microns, 35 microns, etc.), which is administered by rapid inhalation through the nasal passage or by inhalation through the mouth so as to reach the alveolar sacs. Suitable formulations include aqueous or oily solutions of the active ingredient. Formulations suitable for aerosol or dry powder administration may be prepared according to conventional methods and may be delivered with other therapeutic agents such as compounds heretofore used in the treatment or prophylaxis disorders as described below.

Formulations suitable for vaginal administration may be presented as pessaries, tampons, creams, gels, pastes, foams or spray formulations containing in addition to the active ingredient such carriers as are known in the art to be appropriate.

The formulations may be packaged in unit-dose or multi-dose containers, for example sealed ampoules and vials, and may be stored in a freeze-dried (lyophilized) condition requiring only the addition of the sterile liquid carrier, for example water, for injection immediately prior to use. Extemporaneous injection solutions and suspensions are prepared from sterile powders, granules and tablets of the kind previously described. Preferred unit dosage formulations are those containing a daily dose or unit daily sub-dose, as herein above recited, or an appropriate fraction thereof, of the active ingredient.

The invention further provides veterinary compositions comprising a combination described herein together with a veterinary carrier therefore. Veterinary carriers are materials useful for the purpose of administering the composition and may be solid, liquid or gaseous materials which are otherwise inert or acceptable in the veterinary art and are compatible with the active ingredient. These veterinary compositions may be administered parenterally, orally or by any other desired route.

Combination Therapy

The combination may be employed in combination with chemotherapeutic agents for the treatment of a hyperproliferative disease or disorder, including tumors, cancers, and neoplastic tissue, along with pre-malignant and non-neoplastic or non-malignant hyperproliferative disorders. In certain embodiments, a combination is combined in a dosing regimen as combination therapy, with another compound that has anti-hyperproliferative properties or that is useful for treating the hyperproliferative disorder. The additional compound of the dosing regimen preferably has complementary activities to the combination, and such that they do not adversely affect each other. Such compounds may be administered in amounts that are effective for the purpose intended. In one embodiment, the therapeutic combination is administered by a dosing regimen wherein the therapeutically effective amount of a compound GDC-0068 or GDC-0941, or a pharmaceutically acceptable salt thereof is administered in a range from twice daily to once every three weeks (q3 wk), and the therapeutically effective amount of MEHD7945A is administered in a range from twice daily to once every three weeks.

The combination therapy may be administered as a simultaneous or sequential regimen. When administered sequentially, the combination may be administered in two or more administrations. The combined administration includes coadministration, using separate formulation, and consecutive administration in either order, wherein preferably there is a time period while both (or all) active agents simultaneously exert their biological activities.

In one specific aspect of the invention, the GDC-0068 or GDC-0941, or a pharmaceutically acceptable salt thereof can be administered for a time period of about 1 to about 10 days after administration of the MEHD7945A begins. In another specific aspect of the invention, the GDC-0068 or GDC-0941, or a pharmaceutically acceptable salt thereof can be administered for a time period of about 1 to 10 days before administration of the MEHD7945A begins. In another specific aspect of the invention, administration of the compound of GDC-0068 or GDC-0941, or a pharmaceutically acceptable salt thereof and administration of the MEHD7945A begin on the same day.

In one specific aspect of the invention, the MEHD7945A can be administered for a time period of about 1 to about 10 days after administration of the GDC-0068 or GDC-0941, or a pharmaceutically acceptable salt thereof begins. In another specific aspect of the invention, the MEHD7945A can be administered for a time period of about 1 to 10 days before administration of the GDC-0068 or GDC-0941, or a pharmaceutically acceptable salt thereof begins. In another specific aspect of the invention, administration of MEHD7945A and administration of the GDC-0068 or GDC-0941, or a pharmaceutically acceptable salt thereof begin on the same day.

Suitable dosages for any of the above coadministered agents are those presently used and may be lowered due to the combined action (synergy) of the newly identified agent and other chemotherapeutic agents or treatments, such as to increase the therapeutic index or mitigate toxicity or other side-effects or consequences.

In a particular embodiment of anti-cancer therapy, the therapeutic combination may be combined with surgical therapy and radiotherapy. The amounts of the combination and the relative timings of administration will be selected in order to achieve the desired combined therapeutic effect.

Administration of Pharmaceutical Compositions

The compounds may be administered by any route appropriate to the condition to be treated. Suitable routes include oral, parenteral (including subcutaneous, intramuscular, intravenous, intraarterial, inhalation, intradermal, intrathecal, epidural, and infusion techniques), transdermal, rectal, nasal, topical (including buccal and sublingual), vaginal, intraperitoneal, intrapulmonary and intranasal. Topical administration can also involve the use of transdermal administration such as transdermal patches or iontophoresis devices.

Formulation of drugs is discussed in Remington's Pharmaceutical Sciences, 18th Ed., (1995) Mack Publishing Co., Easton, Pa. Other examples of drug formulations can be found in Liberman, H. A. and Lachman, L., Eds., Pharmaceutical Dosage Forms, Marcel Decker, Vol 3, 2nd Ed., New York, N.Y. For local immunosuppressive treatment, the compounds may be administered by intralesional administration, including perfusing or otherwise contacting the graft with the inhibitor before transplantation. It will be appreciated that the preferred route may vary with for example the condition of the recipient. Where the compound is administered orally, it may be formulated as a pill, capsule, tablet, etc. with a pharmaceutically acceptable carrier, glidant, or excipient. Where the compound is administered parenterally, it may be formulated with a pharmaceutically acceptable parenteral vehicle or diluent, and in a unit dosage injectable form, as detailed below.

A dose to treat human patients may range from about 20 mg to about 1600 mg per day of the compound of formula I or II or a pharmaceutically acceptable salt thereof. A typical dose may be about 50 mg to about 800 mg of the compound. A dose may be administered once a day (QD), twice per day (BID), or more frequently, depending on the pharmacokinetic (PK) and pharmacodynamic (PD) properties, including absorption, distribution, metabolism, and excretion of the particular compound. In addition, toxicity factors may influence the dosage and administration dosing regimen. When administered orally, the pill, capsule, or tablet may be ingested twice daily, daily or less frequently such as weekly or once every two or three weeks for a specified period of time. The regimen may be repeated for a number of cycles of therapy.

A dose to treat human patients with an antibody, such as MEHD7945A, may range from about 0.05 mg/kg to about 30 mg/kg. Thus, one or more doses of about 0.5 mg/kg, 2.0 mg/kg, 4.0 mg/kg, 10 mg/kg, 12 mg/kg, 13 mg/kg, 14 mg·kg, 15 mg/kg, 20 mg/kg, 25 mg/kg, or 30 mg/kg (or any combination thereof) may be administered to the patient. Such doses may be administered daily or intermittently, e.g. every week, every two weeks, or every three weeks.

Methods of Treatment

Therapeutic combinations are useful for treating diseases, conditions and/or disorders including, but not limited to, those modulated by AKT kinase in a mammal. Cancers that can be treated according to the methods of this invention include, but are not limited to, mesothelioma, endometrial, glioma, pancreatic, breast (e.g., triple negative breast cancer), lung, ovarian, prostate, melanoma, gastric, colon, and head and neck.

Combinations of the invention may provide improved effects against certain cancer phenotypes. For example, certain combinations of the invention may provide improved effects against cancers associated with PTEN mutation (or low or null status), AKT mutation (or high pAKT expression or amplification levels), PI3K mutation, or a combination of the above.

Accordingly, certain combinations described herein may be particularly useful against these types of cancers.

In one embodiment, the combinations described herein are useful for treating triple negative breast cancer. Triple negative beast cancer is a cancer characterized as being ER-/PR -/HER2-. Triple negative breast cancers account for about 10-20% of all breast cancers and tend to affect younger women. Triple negative breast cancer is very aggressive in nature, and there are limited treatment options.

PTEN null (or low) status may be measured by any suitable means as is known in the art. In one example, IHC is used. Alternatively, Western blot analysis can be used. Antibodies to PTEN are commercially available (Cell Signaling Technology, Beverly, Mass., Cascade Biosciences, Winchester, Mass.). Example procedures for IHC and Western blot analysis for PTEN status are described in Neshat, M. S. et al. Enhanced sensitivity of PTEN -deficient tumors to inhibition of FRAP/mTOR, *Proc. Natl Acad. Sci. USA* 98, 10314-10319 (2001) and Perren, A., et. al. Immunohistochemical Evidence of Loss of PTEN Expression in Primary Ductal Adenocarcinomas of the Breast, *American Journal of Pathology*, Vol. 155, No. 4, October 1999. Additionally, cancers associated with AKT mutation or with PI3K mutation can be identified using techniques that are known in the art.

The level of activation or phosphorylation of AKT ("pAKT") compared to the level of non-activated or non-phosphorylated AKT in a given sample can be measured by methods known in the art. The pAKT status can be expressed in terms of a ratio (e.g. amount of pAKT in a tumor cell divided by amount pAKT in a non-tumorous cell of the same type) or a subtraction (e.g. amount of pAKT in a tumor cell minus amount pAKT in the cell or in a non -tumorous cell of the same type). The pAKT profile can also be expressed in terms of the level of activation of the pathway by measuring amounts of phosphorylated downstream targets of AKT (for example, pGSK or PRAS40). A high pAKT refers to activation or phosphorylation levels of overall AKT in the sample that are higher than a baseline value. In one example, the baseline value is the basal levels of pAKT for a given cell type. In another example, the baseline value is average or mean level of pAKT in a given population of sample cells, for example non-cancerous or cells. In another example, a high pAKT refers to a tumor cell that over-expresses or -amplified phosphorylated or activated AKT in the cell, when compared to an average of normal, healthy (e.g. non-tumorous) cells of the same type from either the same mammal or a patient population. The pAKT profile can also be used in conjunction with other markers, for example FOXO3a localization profiles, for predicting efficacy of certain PI3k/AKT kinase pathway inhibitors. Kits for testing for the presence of PI3k, KRAS and AKT mutations are commercially available (Qiagen).

In one specific aspect, the invention provides a method for treating a patient having a cancer that is associated with PTEN mutation or loss of expression, AKT mutation or amplification, PI3K mutation or amplification, or a combination thereof comprising administering a combination of the invention to the patient. In another aspect, the invention provides a method for identifying a patient having a cancer that that can be treated with a combination of the invention comprising determining if the patient's cancer is associated with PTEN mutation or loss of expression, AKT mutation or amplification, PI3K mutation or amplification, or a combination thereof, wherein association of the patient's cancer with PTEN mutation or loss of expression, AKT mutation or amplification, PI3K mutation or amplification or a combination thereof is indicative of a cancer that can be treated with a combination of the invention. In a further aspect, the invention provides a method further comprising treating the patient so identified with a combination of the invention. In one embodiment, the cancer is ovarian, breast, melanoma, colon or non-small cell lung cancer.

Articles of Manufacture

In another embodiment of the invention, an article of manufacture, or "kit", containing a combination useful for the treatment of the diseases and disorders described above is provided. In one embodiment, the kit comprises a container and a combination described herein.

The kit may further comprise a label or package insert, on or associated with the container. The term "package insert" is used to refer to instructions customarily included in commercial packages of therapeutic products, that contain information about the indications, usage, dosage, administration, contraindications and/or warnings concerning the use of such therapeutic products. Suitable containers include, for example, bottles, vials, syringes, blister pack, etc. The container may be formed from a variety of materials such as glass or plastic. The container may hold a combination, or a formulation thereof, which is effective for treating the condition and may have a sterile access port (for example, the container may be an intravenous solution bag or a vial having a stopper pierceable by a hypodermic injection needle). The label or package insert indicates that the composition is used for treating the condition of choice, such as cancer. In one embodiment, the label or package inserts indicates that the composition comprising the combination can be used to treat a disorder resulting from abnormal cell growth. The label or package insert may also indicate that the composition can be used to treat other disorders. Alternatively, or additionally, the article of manufacture may further comprise a second container comprising a pharmaceutically acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

The kit may further comprise directions for the administration of the combination, and, if present, the second pharmaceutical formulation. For example, if the kit comprises a first composition comprising GDC-0068 or GDC-0941, or a pharmaceutically acceptable salt thereof and a second pharmaceutical formulation comprising MEHD7945A, the kit may further comprise directions for the simultaneous, sequential or separate administration of the first and second pharmaceutical compositions to a patient in need thereof.

In another embodiment, the kits are suitable for the delivery of solid oral forms of a combination, such as tablets or capsules. Such a kit preferably includes a number of unit dosages. Such kits can include a card having the dosages oriented in the order of their intended use. An example of such a kit is a "blister pack". Blister packs are well known in the packaging industry and are widely used for packaging pharmaceutical unit dosage forms. If desired, a memory aid can be provided, for example in the form of numbers, letters, or other markings or with a calendar insert, designating the days in the treatment schedule in which the dosages can be administered.

According to one embodiment, a kit may comprise (a) a first container with GDC-0068 or GDC-0941, or a pharmaceutically acceptable salt thereof contained therein; (b) a second container with MEHD7945A and (c) a third container with a third pharmaceutical formulation contained therein, wherein the third pharmaceutical formulation comprises another compound with anti-hyperproliferative activity. Alternatively, or additionally, the kit may comprise another container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

Where the kit comprises a composition of GDC-0068 or GDC-0941, or a pharmaceutically acceptable salt thereof and MEHD7945A, the kit may comprise a container for containing the separate compositions such as a divided bottle or a divided foil packet, however, the separate compositions may also be contained within a single, undivided container. Typically, the kit comprises directions for the administration of the separate components. The kit form is particularly advantageous when the separate components are preferably administered in different dosage forms (e.g., oral and parenteral), are administered at different dosage intervals, or when titration of the individual components of the combination is desired by the prescribing physician.

SPECIFIC ASPECTS OF THE INVENTION

In one specific aspect of the invention the hyperproliferative disorder is cancer.

In one aspect of the invention the cancer is associated with a hyperactivation of the PI3K/AKT pathway.

In one specific aspect of the invention the cancer is associated with PTEN mutation.

In one specific aspect of the invention the cancer is associated with AKT mutation, overexpression or amplification.

In one specific aspect of the invention the cancer is associated with PI3K mutation.

In one specific aspect of the invention the cancer is associated with a combination of PTEN, AKT and/or PI3K mutation. In one example, the cancer is ovarian, breast, melanoma, head and neck cancer, colon or non-small cell lung cancer.

In one specific aspect of the invention the cancer is selected from, mesothelioma, endometrial, pancreatic, breast (e.g., triple negative breast cancer), lung, ovarian, prostate (e.g. castration resistant prostate cancer), melanoma, gastric, colon, renal, head and neck, and giloma.

EXAMPLES

In order to illustrate the invention, the following examples are included. However, it is to be understood that these examples do not limit the invention and are only meant to suggest a method of practicing the invention.

Example 1

Combined Blockade of PI3K/AKT and HER3/EGFR Enhances Anti-Tumor Activity in Triple Negative Breast Cancer Up to 60% of triple negative breast cancers (TNBCs) express high levels of EGFR. Moreover, TNBCs are associated with increased frequency of phosphatase and tension homologue (PTEN) loss of function, leading to hyperactivation of the phosphoinositide 3-kinase (PI3K)/AKT pathway. This provides the rationale for using PI3K/AKT inhibitors in this subset of patients. However, compensatory expression of receptor tyrosine kinases (RTKs) such as HER3 can limit efficacy of PI3K/AKT inhibitors. Whether combined targeting of both EGFR and HER3 and the PI3K/AKT pathway results in superior antitumor activity compared to single agent in TNBC was evaluated.

Several TNBC cell lines were treated with MEHD7945A, a dual-action antibody that targets both EGFR and HER3, AKT inhibitor GDC-0068, and pan-PI3K inhibitor GDC-0941. Cell viability was measured by CellTiter-Glo and Crystal Violet. Both cell line- and patient-derived xenograft models of TNBC were treated with MEHD7945A, GDC-0068, GDC-0941, or the combination of MEHD7945A with either GDC-0068 or GDC-0941. Tumor size and histology were examined. Protein expression was measured by Western blot, Mass Spectometry, CEER and immunohistochemistry.

GDC-0068 and GDC-0941 treatment resulted in variable inhibition of cell viability, with IC50s ranging from 170 nM to >1 μM across all TNBC cell lines. In cells stimulated with either EGF or Heregulin, MEHD7945A prevented HER3/EGFR receptor phosphorylation and improved the antiproliferative activity of the PI3K inhibitors.

To test the activity of these compounds in vivo, three different models of TNBC were used: two cell line (MDA-MB-468 and HCC70)-based and a patient-derived xenograft. Administration of MEHD7945A, GDC-0941 or GDC-0068 showed variable delay in tumor growth whereas a combination of MEHD7945A with either GDC-0068 or GDC-0941 was superior to single agent treatment. Both combinations either prevented tumor growth or led to tumor shrinkage with complete responses achieved in ½ of the mice in each cohort. Of note, all the treatments (up to 9 weeks of therapeutic exposure) were well tolerated. Analysis of treated tumors revealed potent inhibition of the PI3K/AKT pathway, with decreased levels phospho-PRAS40 and phospho-S6. Moreover, MEHD7945A effectively prevented EGFR and HER3 phosphorylation consequent to PI3K inhibition.

Provided herein is evidence that HER3 plays a role in limiting the antitumor activity of both PI3K/Akt inhibitors and anti-EGFR agents. Simultaneous targeting of EGFR and HER3 by MEHD7945A enhances the efficacy of PI3K/Akt inhibition in preclinical models of EGFR-positive TNBC. Further, HER3 expression appears to be induced in TNBC patients with a lower probability of achieving tumor regression upon anti-EGFR therapy. Simultaneous inhibition of EGFR, HER3 and the PI3K/Akt pathway has the potential to greatly expand the percentage of TNBC patients who can benefit from targeted therapy.

As such, combined therapy with MEHD7945A and either GDC-0068 or GDC-0941 was superior to monotherapy in preclinical models of TNBC.

Results

Figure 1:
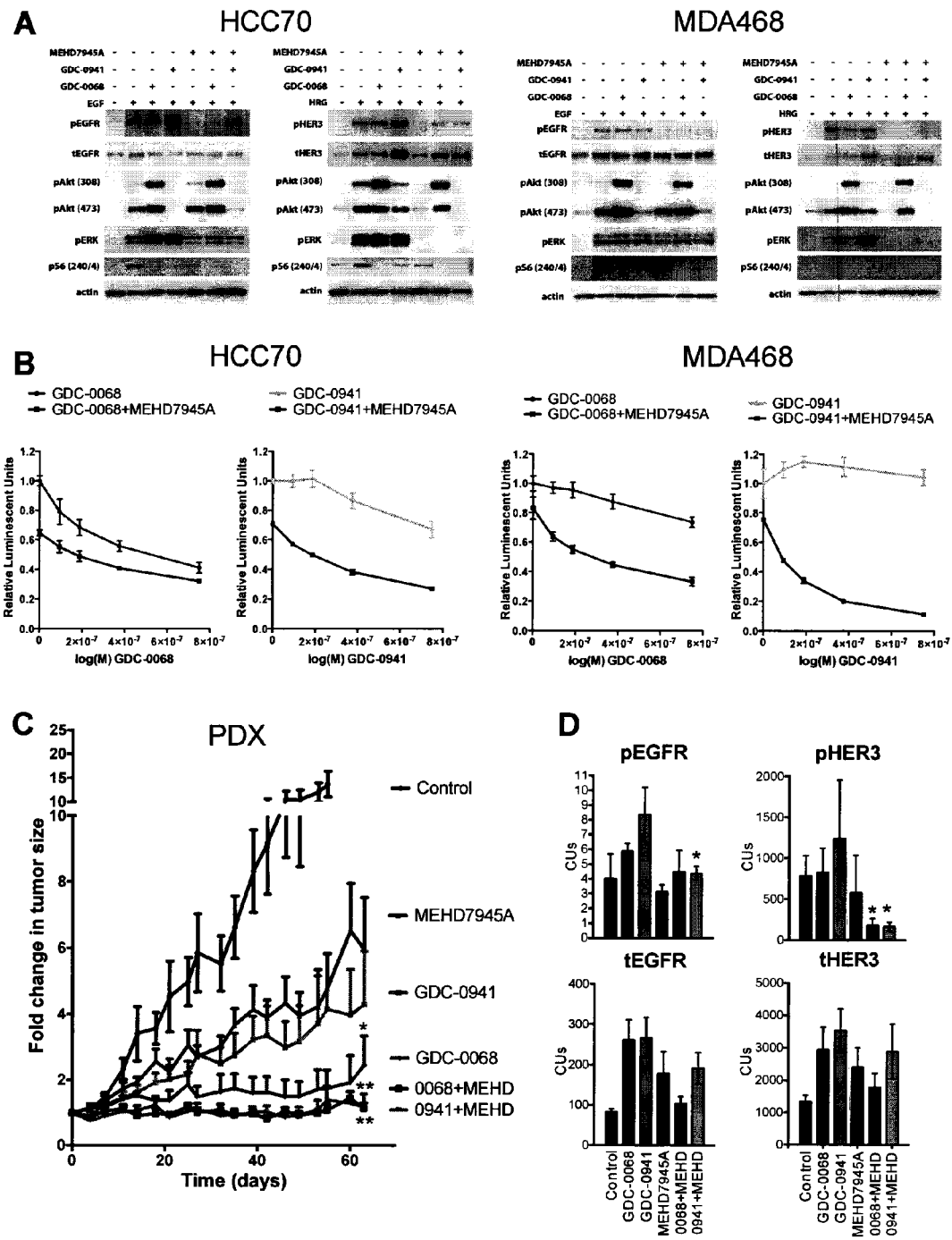
FIG. 1. Therapeutic activity of combined inhibition of EGFR, HER3 and the PI3K/Akt pathway in TNBC preclinical models. (A) Western blot showing expression and activation of EGFR, HER3 and downstream signaling pathways following the indicated treatment for 24 hours. MEHD7945A was used at 10 nM while both GDC-0068 and GDC-0941 at 1 uM. (B) Five days proliferation analyses of MDA-MB-468 and HCC70 cells treated as indicated. MEHD7945A was used at 10 nM while both GDC-0068 and GDC-0941 at 1 uM. (C) Tumor growth curves of TNBC patient-derived xenografts (PDX) treated as indicated. MEHD7945A was given 10 mg/Kg twice weekly, GDC-0941 75 mg/Kg daily and GDC-0058 40 mg/Kg daily. (D) CEER analysis of active and total EGFR and HER3 in PDXs treated as indicated. Tumors were harvested 2 h after the last drug administration. Proteins were normalized versus the amount of total cytokeratins to avoid signal from stromal contamination and quantified by computational units (CUs). Error bars show SEM combinations GDC-0068 or GDC-0941 and MEHD7945A versus single agents; *$p<0.05$, **$p<0.01$. P-value was calculated using two-sided student's t-test.

Blockade of EGFR and HER3 Combined with PI3K/Akt Inhibition Results in Superior Antitumor Activity HCC70 and MDA-MB-468 TNBC cell lines, characterized by elevated levels of EGFR and loss of PTEN expression, were treated with GDC-0068, GDC-0941, MEHD7945A, and the combinations of these inhibitors. Treatment with either GDC-0068 or GDC-0941 resulted in increased expression of HER3 and, in HCC70 cells, activation of both EGFR and HER3 (FIG. 1A). The addition of MEHD7945A prevented the induction of EGFR and HER3 phosphorylation and enhanced the inhibition of the PI3K and ERK downstream pathways in both cell lines (FIG. 1A). Of note, GDC-0068 competes for the ATP-binding site of Akt and can cause hyperphosphorylation of the enzyme at its two regulatory sites (Thr308 and Ser473 (Okuzumi et al., Nat Chem Biol 5, 484 (2009)).

Whether the combination of MEHD7945A with GDC-0068 or GDC-0941 would result in enhanced antiproliferative activity was tested in both HCC70 and MDA-MB-468 cells. In cells treated for 5 days, varying sensitivity to the single-agents GDC-0068, GDC-0941 and MEHD7945A was observed. However, the combination of the anti-PI3K/Akt agents and MEHD7945A led to superior inhibition of cell proliferation/viability compared to single agents (FIG. 1B).

To expand these findings in vivo, the efficacy of MEHD7945A was tested in combination with either the Akt or PI3K inhibitor in both MDA-MB-468- and HCC70-derived xenografts. While the tumors responded only modestly to single agent GDC-0068, GDC-0941 and MEHD7945A, the combination of GDC-0068 or GDC-0941 and MEHD7945A yielded significantly superior tumor growth inhibition compared to monotherapy (p less than 0.01, P-value was calculated using two-sided student's t-test). Moreover, 9 out of 19 mice in the combination cohorts achieved complete tumor shrinkage, with no relapses observed 90 days after treatment cessation.

The levels of EGFR and HER3 expression/activation in HCC70 tumors collected at the end of the experiments (day 39) was investigated. The technical challenge of obtaining reliable phospho-HER3 (pHER3) detection by immunohistochemistry (IHC) and the relatively low amount of tissue available from the tumors treated with the combination regimens prompted the measurement of both HER3 expression and phosphorylation using an alternative methodology. Frozen tissue was analyzed by Cooperative, Enhanced, Enzyme Immunoreactive (CEER), a platform that utilizes reverse-phase detection of nanogram quantities of protein. Akt or PI3K inhibition led to an overall increase of both EGFR and HER3 expression and phosphorylation (p less than 0.05, P-value was calculated using two-sided student's t-test). While not intending to be limited to this interpretation, the rise in EGFR phosphorylation following GDC-0068 was most likely a result of increased EGFR/HER3 heterodimerization, as no changes in the total receptor levels were observed. The addition of MEHD7945A to either GDC-0068 or GDC-0941 reduced receptor phosphorylation induced by PI3K/Akt.

The activity of the same treatments in patient-derived xenografts (PDX) of TNBC was then tested. These tumors were characterized by IHC, which found undetectable levels of PTEN, high levels of EGFR and ~70% staining for Ki67. These features predicted a particularly aggressive phenotype, confirmed by the rapid growth of the untreated tumor xenografts (FIG. 1C, control arm). Both single agent GDC-0941 and MEHD7945A delayed tumor growth. In combination, they caused durable tumor stasis (FIG. 1C). Consistent with the cell-based xenografts, both active and total levels of HER3 and EGFR increased upon PI3K/Akt inhibition and MEHD7945A prevented receptor phosphorylation (FIG. 1D). Interestingly, GDC-0068 monotherapy showed superior antitumor activity compared with GDC-0941. This effect may be due to its lower ability to induce EGFR and HER3 phosphorylation in this model (FIG. 1D). Nonetheless, its efficacy was further enhanced by the addition of MEHD7945A.

Tumor cell proliferation was measured using the Ki67 index in specimens from xenografts collected at the experimental endpoints. The percentage of Ki67-positive cells was significantly lower only in the combination cohorts. These results were further confirmed measuring the number of Ki67-positive circulating tumor cells (CTCs) in mice bearing established patient-derived tumors of >1 $cm^3$ volume and treated for 6 days with GDC-0941, MEHD7945A or the combination of both agents. The treatments were well tolerated for the entire duration of the experiments, and no tumor relapse was detected in the mice that experienced complete tumor regression. Collectively, these data show that targeting both EGFR and HER3 enhances the antitumor effects of PI3K/Akt inhibitors.

Figure 2:
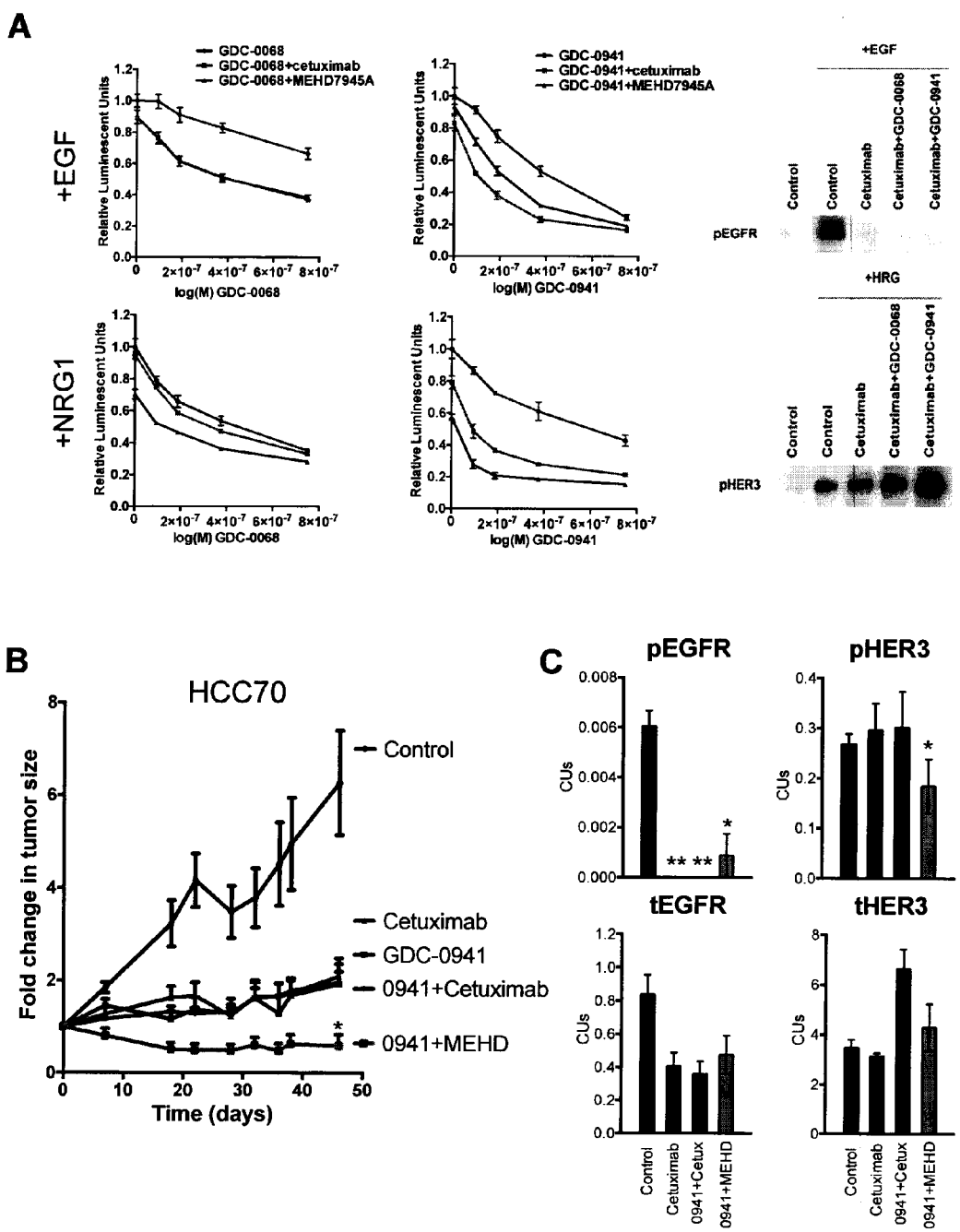
FIG. 2. Efficacy of MEHD7945A or cetuximab in combination with PI3K inhibition. (A) Left: Five days proliferation analyses of HCC70 cells treated as indicated. MEHD7945A and cetuximab were used at 10 nM while both GDC-0068 and GDC-0941 at 1 uM. Right: Western blot showing expression of pEGFR and pHER3 in HCC70 cells treated as indicated. (B) Tumor growth curves of HCC70 xenografts treated as indicated. MEHD7945A and cetuximab were given 10 mg/Kg twice weekly and GDC-0941 75 mg/Kg daily. Error bars show SEM combinations GDC-0941 and MEHD7945A versus single agents or combination GDC-0941 and cetuximab; *$p<0.05$. (C) CEER analysis of active and total EGFR and HER3 in HCC70 xenografts treated as indicated. Error bars show SEM of all conditions versus control for pEGFR (**$p<0.01$) and combinations GDC-0068 and MEHD7945A versus combination GDC-0941 and cetuximab or cetuximab single agent (*$p<0.05$). P-value was calculated using two-sided student's t-test.

HER3 Suppression is Required for Optimal Antitumor Activity Mediated by PI3K/Akt Inhibition In order to dissect the roles of HER3 inhibition in these models, the activity of cetuximab, an antibody targeting exclusively EGFR, with MEHD7945A in combination with either GDC-0068 or GDC-0941 in HCC70 cells was determined. Both antibodies enhanced the antiproliferative activity mediated by PI3K/Akt inhibition in cells stimulated with epidermal growth factor (EGF). However, MEHD7945A was superior to cetuximab in cooperating with the antiproliferative activity of GDC-0068 and GDC-0941 in cells stimulated with heregulin (HRG) (FIG. 2A).

The antitumor activity of cetuximab and MEHD7945A in combination with GDC-0941 in HCC70-derived xenografts was determined. While the combination of cetuximab and GDC-0941 did not lead to any further inhibition of tumor growth compared to single agent treatments, concomitant targeting of EGFR, HER3 and PI3K led to tumor shrinkage (FIG. 2B) with complete regression of the xenografts in 4 out of 9 cases. Biochemically, both MEHD7945A and cetuximab blocked EGFR phosphorylation in these xenografts; however, only MEHD7945A decreased HER3 activation (FIG. 2C). These results confirm that HER3 plays an important role in limiting the efficacy of PI3K inhibition in this setting.

EGFR Downregulation and HER3 Upregulation are Associated with Lower Response to Anti-EGFR Therapy in TNBC Patients To investigate whether changes in EGFR and HER3 can affect the response to targeted therapy in the clinic, the expression of these receptors was measured in samples from TNBC patients enrolled in two pilot neoadjuvant clinical trials testing the antitumor activity of the anti-EGFR antibodies panitumumab (40 patients) and cetuximab (30 patients) in combination with standard chemotherapy.

Of 40 patients enrolled in the study that combined panitumumab with 4 standard cytotoxic agents, 19 (47.5%) achieved pathological complete response (pCR) (24 weeks) and 21 (52.5%) showed residual disease at the time of surgery. This two-fold increase in pCR compared to TNBC patient treated only with cytotoxics-based neoadjuvant chemotherapy (C. Liedtke et al., *Journal of Clinical Oncology: Official Journal of the American Society of Clinical Oncology* 26, 1275 (2008)) underscores the benefit of adding anti-EGFR therapy in this setting. IHC assessment of EGFR and HER3 expression was performed in all the pre-treatment specimens and in the 21 residual invasive tumors excised at surgery. The group of patients with a pre-treatment EGFR histoscore more than 70 demonstrated a pCR rate of 58% (15 out of 26) while complete tumor regression was limited to 28% (4 out of 14) in those patients with a pre-treatment EGFR histoscore ≤70 (FIG. 3A). This trend, however, did not reach statistical significance (p=0.08), probably a reflection of the small number of patients analyzed.

The levels of EGFR of the residual (post-treatment) tumors from the patients that did not experience pCR was compared to their pre-treatment counterparts. EGFR levels were decreased in the residual tumors of nine out of 21 non-pCR patients when compared to the paired baseline specimens (FIGS. 3B and C, p equals 0.07).

The levels of HER3 were measured in the residual (post-treatment) tumors from the patients that did not experience pCR to their pre-treatment counterparts. HER3 immunostaining, available for 13 non-responder patients, showed higher HER3 expression in the residual lesions of 7 out of 13 non-pCR patients compared to the paired pre-treatment samples (FIGS. 4A and B, p equals 0.010).

Of 30 patients enrolled in the study testing the antitumor activity cetuximab combined with docetaxel, 9 experienced pCR. Consistently, HER3 expression was found upregulated in the residual tumors of 11 out of 19 non-pCR patients when compared to the baseline paired specimens (p equals 0.103).

These results indicate that 1) high EGFR expression may be required for optimal response to anti-EGFR therapeutic antibodies and that 2) HER3 expression increases following anti-EGFR therapy in patients that do not experience complete tumor regression. As such, these discoveries provide biomarkers for therapeutic treatment. For example, patient selection may be based on high EGFR expression with "on-treatment" biopsies to evaluate both pathway inhibition and possible RTK upregulation upon therapy. Patients having TNBC can be screened for EGFR expression, and those patients having relatively elevated EGFR expression can be selected for the treatments described herein. HER3 expression can also be determined in patients receiving treatment to identify those patients having relatively elevated HER3 expression as at an elevated risk for lack of complete tumor regression.

Materials and Methods

Study Design

An objective of this study was to test the activity of concomitant blockade of EGFR, HER3 and the PI3K/Akt pathway in preclinical models of TNBC. Moreover, whether the expression of both EGFR and HER3 were influencing the clinical response to anti-EGFR therapy in TNBC patients was assessed.

The size of the animal groups was calculated in order to measure means difference between placebo and treatment groups of 25% with a power of 80% and a p value of 0.01. Host mice carrying xenografts were randomly and equally assigned to either control or treatment groups. Animal experiments were conducted in a controlled and non-blinded manner. Quantification of pS6 (240-4) in patient samples was performed in a blinded manner. In vitro experiments were performed at least two times and at least in triplicate for each replica.

Cell Lines and Chemical Compounds

MDA-MB-468 and HCC70 were purchased from ATCC and maintained at 37° C. in Dulbecco's Modified Eagle's Media (DMEM):Ham's F-12 1:1 and RPMI 1640 respectively, with 10% fetal calf serum (FCS), 2 mmol/L 1-glutamine, 20 units/ml penicillin and 20 μg/ml streptomycin in a humidified atmosphere and 5% CO2. The pan-PI3K inhibitor, GDC-0941, was obtained from the SU2C/PI3K Dream Team mouse pharmacy. The Akt inhibitor, GDC-0068, and dual EGFR-HER3 inhibitor, MEHD7945A, were kindly provided by Genentech. All compounds were dissolved in dimethyl sulfoxide (DMSO) for in vitro experiments.

Cell Viability and Proliferation

For proliferation, $5 \times 10^5$ cells were seeded in 96-well plates and treated with the indicated concentrations of GDC-0068, GDC-0941, and/or MEHD7945A. After 5 days, cells were fixed and stained with Crystal Violet. Cell proliferation was also analyzed with CellTiter-Glo Luminescent Cell Viability Assay (Promega) as described by the manufacturer. For heregulin (HRG, Peprotech) and epidermal growth factor (EGF, Peprotech)-induced proliferation, $5 \times 10^5$ cells were treated with GDC-0068, GDC-0941, and/or MEHD7945A in the presence of 4 ng/ml of ligands for 5 days and then stained with Crystal Violet.

Western Blotting

Cells were washed with ice-cold phosphate buffered saline (PBS) and scraped into ice-cold RIPA lysis buffer (Cell Signaling) supplemented with phosphatase inhibitor cocktails (Complete Mini, and PhosphoStop (Roche)). Lysates were cleared by centrifugation at 13,000 rpm for 10 minutes at 4° C., supernatants removed and assayed for protein concentration using the Pierce BCA Protein Assay Kit (Thermo Scientific). Thirty-five micrograms of total lysate was resolved on NuPAGE 4-12% Bis-Tris gels (Life Technologies) and electrophoretically transferred to Immobilon transfer membranes (Millipore). Membranes were blocked for 1 hour in 5% nonfat dry milk in TBS-Tween and then hybridized using the following primary antibodies in 5% bovine serum albumin (BSA) TBS-Tween: phospho-Akt (Ser473), phospho-Akt (Thr308), Akt, phospho-S6 (Ser (240/4), phospho-S6 (Ser235/6), S6, phospho-PRAS40 (Thr246), PRAS40, phospho-Erk (Thr202/Tyr204), Erk, phospho-EGFR (Tyr1068), EGFR, phospho-HER3 (Tyr1289), HER3 (1:500-1:1000, Cell Signaling). Beta-actin was used as a loading control (1:5000, Sigma), also in 5% BSA TBS-Tween. Mouse and rabbit horseradish peroxidase (HRP)-conjugated secondary antibodies (1:50,000, Amersham Biosciences) were diluted in 2% nonfat dry milk in TBS-Tween. Protein—antibody complexes were detected by chemiluminescence with SuperSignal West Femto-Chemiluminescent Substrate (Thermo Scientific) and images were captured with a G-BOX camera system.

Establishment of Tumor Xenografts and In Vivo Treatments

All mouse studies were conducted through institutional Animal Care and Use Committee (IACUC) approved animal protocols in accordance with institutional guidelines. Six-week-old female athymic nude mice were purchased from Charles River Laboratories and housed in air-filtered laminar flow cabinets with a 12-hour light cycle and food and water ad libitum.

For cell line-derived xenograft studies, mice were injected subcutaneously with $1 \times 10^7$ HCC70 or MDA-MB-468 suspended in 150 µL culture media/Matrigel (BD Biosciences) in a 4:1 ratio. One µmol/L of 17β-estradiol was supplemented in the mouse drinking water as described (Garcia-Garcia et al., *Clinical cancer research: an official journal of the American Association for Cancer Research* 18, 2603 (2012)).

For patient-derived xenograft (PDX) studies, tumors were subcutaneously implanted in 6-week old female athymic nude mice. Upon xenograft growth, tumor tissue was reimplanted into recipient mice, which were randomized upon implant growth. For the collection of circulating tumor cells (CTCs), tumors were implanted into the mammary pad of athymic nude mice.

Once tumors reached an average volume of about 150-250 mm³, mice were randomized into treatment arms, with n=7-11 tumors/group. GDC-0068 [40 mg/kg] or GDC-0941 [75 mg/kg] were dissolved in 0.5% methylcellulose and 0.2% Tween-80 (MCT) solution and administered once daily via oral gavage. MEHD7945A [10 mg/kg] and cetuximab [10 mg/kg] were diluted in PBS and injected intraperitoneally twice weekly. Tumors were measured by digital caliper over the entire treatment period. Tumor volume was determined using the formula: (length×width²)×(π/6). Tumor volumes are plotted as means±SEM.

Cooperative, Enhanced, Enzyme Immunoreactive (CEER) Assay

The levels of pathway protein expression and their activation in xenografts were determined by CEER. (Kim et al., *ASCO Annual Meeting abstract* P2-06-13, (2010)) CEER utilizes the formation of unique immuno-complexes between capture antibodies printed on a nitrocellulose microarray surface, the target molecule in cell lysate reacted with the slide, and two independent detector-antibodies. One of the detector-antibody is conjugated to glucose oxidase, and the other is conjugated to horseradish peroxidase. Target detection (expressed as computational unit, CU) requires the presence of both detector-antibodies and the enzyme channeling event between glucose oxidase and horseradish peroxidase will not occur unless both antibodies are in close proximity.

Circulating Tumor Cells (CTCs)

Circulating tumor cells (CTCs) were captured on the herringbone-chip, fixed and permeabilized as previously described (Stott et al., *Proceedings of the National Academy of Sciences* 107, 18392 (2010)). For capture, the herringbone-chip was coated with anti -EpCAM (R&D Systems) and anti-EGFR (cetuximab, Eli Lilly) antibodies. The chip with CTC was incubated with primary antibodies against wide-spectrum cytokeratins (Abcam), CD45 (Santa Cruz Biotechnology) and Ki67 (Life Technologies) and secondary antibodies conjugated with Alexa Fluor 647, Alexa Fluor 555 and Alexa Fluor 488 (all from Life Technologies). Nuclei were stained with DAPI. An automated fluorescence microscopy scanning system (BioView) was used to identify Ki67-positive CTCs ($CK^+/CD45^-/Ki67^+$), Ki67-negative CTCs ($CK^+/CD45^-/Ki67^-$) and contaminating white blood cells ($CD45^+$).

Immunohistochemistry (IHC)

Xenografts: Dissected tissues were fixed immediately after removal in a 10% buffered formalin solution for a maximum of 24 h at room temperature (RT) before being dehydrated and paraffin-embedded under vacuum conditions. Samples were blocked with normal goat serum, and incubated with Ki67 (Life Technologies), EGFR (Cell Signaling) and PTEN (Cell Signaling) antibodies. The antigen-antibody reaction was revealed by SignalStain® Boost IHC Detection Reagent (Cell Signaling 8114) with DAB as substrate (Dako).

Patient samples: Tumor tissue was fixed in 10%-buffered formalin for 48 h and further embedded in paraffin. Four-micron sections were deparaffinized in xylene and hydrated in graded alcohols. For EGFR detection, the antigen was retrieved by protease treatment (8 min at 37° C.) and the sections further incubated at 37° C. for 1 h with pre-diluted, ready-to-use mouse monoclonal anti-EGFR (clone 3C6, Ventana, Tucson, Ariz.). The antigen-antibody reaction was visualized by UltraView DAB reveal system in a Benchmark XT automated IHC stainer (all from Ventana). For HER3, the antigen retrieval was performed by heating the sections at 97° C. for 20 min in EnVision® Target Retrieval Solution High pH (Dako) in PT-Link apparatus (Dako). The tissues were then incubated at 37° C. for 2 h with mouse monoclonal anti-HER3 (clone DAK-H3-IC, Dako, Glostrup, Denmak) diluted at 1:50. The antigen-antibody reaction was revealed using EnVision® Flex DAB system in a Dako Autostainer Plus automate. For each patient the pre-treatment and the post-treatment tumor sample were run together. IHC staining was interpreted by an expert pathologist who was blind to patient information. Both EGFR and HER3 expressions were quantified using an arbitrary scale having 0, 0.5, 1, 1.5, 2, 2.5 and 3 as measures of increasing staining intensity. EGFR and HER3 histoscores were defined as a sum of products obtained by multiplying the staining intensity with the percentage of stained cells.

Patient Samples

For PDX establishment, fresh tissue was obtained from the Massachusetts General Hospital under Institutional Review Board-approval and patient's informed consent. Triple negative status was determined by the Massachusetts General Hospital Clinical Laboratory and Department of Pathology.

FFPE specimens for IHC analyses of EGFR and HER3 expression were obtained from the institutions participating in two French multicenter pilot phase II neoadjuvant trials which tested the efficacy of an anti-EGFR antibody combined to chemotherapy in TNBC stage II-IIIA pts. One trial regimen consisted of 8 cycles, administered each 3 weeks. First 4 cycles contained 9 mg/kg of panitumumab combined with 500 mg/m2 of each 5-fluorouracil and cyclophosphamide plus 100 mg/m2 of epirubicin. Last 4 cycles had panitumumab with 100 mg/m2 docetaxel instead of 3 cytotoxics previously mentioned. Another trial regimen contained weekly cetuximab (first dose of 400 mg/m2, with all the following doses of 250 mg/m2) associated to 100 mg/m2 docetaxel given each 3 weeks for a total of 6 cycles. All patients underwent surgery at completion of treatment. Pathologic complete response (pCR) was the primary endpoint with clinical response and toxicity as secondary endpoints. Forty patients have been eligible for the pathologic response evaluation and biomarker studies in the panitumumab trial, while the cetuximab trial ended with 30 eligible pts. Tumor tissue samples were systematically collected before and at the end of the neoadjuvant treatment and collection was centralized at the Jean Perrin Comprehensive Cancer Center where molecular and pathological analyses were performed. pCR was evaluated using Chevallier's (Chevallier et al., *American Journal of Clinical Oncology* 16, 223 (1993)) and Sataloff's (Sataloff et al., *Journal of the American College of Surgeons* 180, 297 (1995)) classifications.

Statistical Analysis

Two-way t-test was done using GraphPad Prism (GraphPad Software). Error bars represent the SEM. *$p<0.05$, **$p<0.01$. All the in vitro experiments were repeated at least three times. All the in vivo experiments were run with at least n=7 for each treatment arm.

All documents cited herein are incorporated by reference. While certain embodiments of invention are described, and many details have been set forth for purposes of illustration, certain of the details can be varied without departing from the basic principles of the invention. Since numerous modifications and changes will be readily apparent to those skilled in the art, it is not desired to limit the invention to the exact construction and process shown as described herein. Accordingly, all suitable modifications and equivalents may be considered to fall within the scope as defined by the claims that follow.

What is claimed is:

1. A method for treating triple negative breast cancer associated with PTEN mutation in a mammal comprising, administering to the mammal a combination of GDC-0068, or a pharmaceutically acceptable salt thereof, and MEHD7945A.

2. A method for treating triple negative breast cancer associated with PTEN mutation modulated by AKT kinase in a mammal comprising, administering to the mammal a combination of GDC-0068 or a pharmaceutically acceptable salt thereof, and MEHD7945A.

3. The method of claim 1, wherein the cancer is associated with AKT mutation, overexpression or amplification.

4. The method of claim 1, wherein the cancer is associated with PI3K mutation.

5. The method of claim 1, wherein GDC-0068, or a pharmaceutically acceptable salt thereof is administered simultaneously with MEHD7945A.

6. The method of claim 1, wherein GDC-0068, or a pharmaceutically acceptable salt thereof and MEHD7945A are administered sequentially.

7. The method of claim 1, wherein the mammal is a human having triple negative breast cancer (TNBC) that has been selected for treatment as having TNBC with elevated EGFR expression.

8. The method of claim 1, wherein HER3 expression is measured following the treatment, wherein relatively elevated HER3 expression indicates an elevated risk for lack of complete tumor regression.

* * * * *

UNITED STATES PATENT AND TRADEMARK OFFICE
CERTIFICATE OF CORRECTION

PATENT NO.         : 9,566,334 B2
APPLICATION NO.    : 14/649889
DATED              : February 14, 2017
INVENTOR(S)        : Jose Baselga and Maurizio Scaltriti Page 1 of 1

It is certified that error appears in the above-identified patent and that said Letters Patent is hereby corrected as shown below:

In the Claims

Column 35, Line 31, Claim 21, please delete "combination of GDC-0068or a" and insert
-- combination of GDC-0068, or a -- therefor.

Signed and Sealed this
Twenty-fourth Day of October, 2017

Joseph Matal
*Performing the Functions and Duties of the*
*Under Secretary of Commerce for Intellectual Property and*
*Director of the United States Patent and Trademark Office*